US008388931B2

(12) United States Patent
Lopez et al.

(10) Patent No.: US 8,388,931 B2
(45) Date of Patent: Mar. 5, 2013

(54) 99M TC-LABELED TRIPHENYLPHOSPHONIUM DERIVATIVE CONTRASTING AGENTS AND MOLECULAR PROBES FOR EARLY DETECTION AND IMAGING OF BREAST TUMORS

(76) Inventors: Marcos Lopez, Wauwatosa, WI (US); Micael Joel Hardy, La Seyne sur mer (FR); Balaraman Kalyanaraman, Wauwatosa, WI (US); Ming Zhao, Brookfield, WI (US)

( * ) Notice: Subject to any disclaimer, the term of this patent is extended or adjusted under 35 U.S.C. 154(b) by 755 days.

(21) Appl. No.: 12/394,581

(22) Filed: Feb. 27, 2009

(65) Prior Publication Data
US 2009/0220419 A1    Sep. 3, 2009

Related U.S. Application Data

(60) Provisional application No. 61/032,913, filed on Feb. 29, 2008.

(51) Int. Cl.
*A61K 51/00* (2006.01)
*A61M 36/14* (2006.01)
(52) U.S. Cl. ............ 424/1.69; 424/1.11; 424/1.53; 424/1.61; 424/1.65; 424/9.2
(58) Field of Classification Search .......... 424/1.69
See application file for complete search history.

(56) References Cited

U.S. PATENT DOCUMENTS

| | | | |
|---|---|---|---|
| 4,142,102 | A | 2/1979 | Lange |
| 4,639,365 | A | 1/1987 | Sherry |
| 5,337,231 | A | 8/1994 | Nowak |
| 2004/0033197 | A1 * | 2/2004 | Madar et al. ............ 424/9.1 |
| 2007/0066572 | A1 | 3/2007 | Balaraman et al. |
| 2007/0225255 | A1 | 9/2007 | Frohlich et al. |

FOREIGN PATENT DOCUMENTS

WO    8911475 A1    11/1989

OTHER PUBLICATIONS

Wang et al. Nat. Protocols, 2007, 972-978.*
Arbab A et al., Uptake of Technetium-99m-Tetrofosmin, Tecnetium-99m-MIBI and Thallium-201 in Tumor Cell Lines, J Nucl Med 1996, 37:1551-1556.
Asin-Cayuela J et al., Fine-tuning the hydrophobicity of a mitochondria-targeted antioxidant, FEBS Lett 2004, 571:9-16.
Ballinger J, 99mTc-Tetrofosmin for Functional Imaging of P-glycoprotein Modulation In Vivo, J Clin Pharmacol 2001, 41:39S-47S.
Berge SM et al., Pharmaceutical Salts, J. Pharm. Sci. 66:1-19 (1977).
Brem R et al., Breast-specific Gamma Imaging as an Adjunct Imaging Modality for the Diagnosis of Breast Cancer, Radiology 2008, 247(3):651-657.
Brem R et al., Occult Breast Cancer: Scintimammography with High-Resolution Breast-specific Gamma Camera in Women at High Risk for Breast Cancer, Radiology 2005, 237:274-280.
Brem R et al., High-Resolution Scintimammography: A Pilot Study, J Nucl Med 2002, 43:909-915.
Cooper W et al., 1H NMR Visible Lipids Are Induced by Phosphonium Salts and 5-Fluorouracil in Human Breast Cancer Cells, Magnetic Resonance in Med 2001, 45:1001-1010.
Delmon-Moingeon L et al., Uptake of the Cation Hexakis(2-methoxyisobutylisonitrile)-Technetium-99m by Human Carcinoma Cell Lines in Vitro, Canc Res 1990, 50:2198-2202.
Foster P. et al., A New Therapeutic Strategy against Hormone-Dependent Breast Cancer: The Preclinical Development of a Dual Aromatase and Sulfatase Inhibitor, Clin Cancer Res 2008, 14(20):6469-6477.
Haynes DA et al., Occurrence of Pharmaceutically Acceptable Anions and Cations in the Cambridge Structural Database, J Pharm Sci 94:2111-2120 (2005).
Hussain R et al., A Meta-analysis of Scintimammography: an Evidence-based Approach to its Clinical Utility, Nu Med Comm 2006, 27:589-594.
Jemal, A. et al., Cancer Statistics, 2004, CA Cancer J Clin 2004, 54:8-29.
Khalkhali I et al., 99mTc Sestamibi Breast Imaging for the Examination of Patients with Dense and Fatty Breasts: Multicenter Study, Radiology 2002, 222:149-155.
Khalkhali I et al., Scintimammography: The Complementary Role of Tc-99m Sestamibi Prone Breast Imaging for the Diagnosis of Breast Carcinoma, Radiology 1995, 196:421-426.
Kim et al., Effects of Targeting Moiety, Linker, Bifunctional Chelator, and Molecular Charge on Biological Properties of 64Cu-Labeled Triphenylphonium Cations, J Med Chem 2008, 51:2971-2984.
Kroemer G, Mitochondria in Cancer, Oncogene 2006, 25:4630-4632.
Liberman M et al., Breast Cancer Diagnosis by Scintimammography: a Meta-analysis and Review of the Literature, Breast Canc Res Treat 2003, 80:115-126.
Mathieu I et al., Inconclusive Triple Diagnosis in Breast Cancer Imaging: Is There a Place for Scintimammography?, J Nucl Med 2005, 46:1574-1581.
Nandi S et al., Hormones and Mammary Carcinogenesis in Mice, Rats, and Humans: A Unifying Hypothesis, Proc Natl Acad Sci USA 1995, 92:3650-3657.
Papantoniou V et al., The Potential Role of Calcitonin Gene-Related Peptide (CGRP) in Breast Carcinogenesis and Its Correlation With 99mTc-(V)DMSA Scintimammography, Am J of Clinical Oncology 2007, 30(4)420-427.
Parker S et al., Cancer Statistics, 1997, CA Cancer J Clin 1997, 47:5-27.

(Continued)

*Primary Examiner* — Michael G Hartley
*Assistant Examiner* — Sean R Donohue
(74) *Attorney, Agent, or Firm* — Quarles & Brady LLP

(57) ABSTRACT

$^{99m}$Tc-labeled triphenylphosphonium contrasting agents that target the mitochondria and are useful for early detection of breast tumors using scintimammographic imaging. $^{99m}$Tc-Mito$_{10}$-MAG3 possesses advantageous radiopharmaceutical properties. The uptake in the myocardium is reduced by one to two orders of magnitude compared to $^{99m}$Tc-MIBI. $^{99m}$Tc-Mito$_{10}$-MAG3 exhibits fast blood clearance, with a blood half-life of less than 2 minutes in rats. A diminished myocardial uptake combined with a prompt reduction of cardiovascular blood pool signal to facilitate improved signal-to-background ratios.

5 Claims, 9 Drawing Sheets

OTHER PUBLICATIONS

Piwnica-Worms D et al., Functional Imaging of Multidrug-resistant P-Glycoprotein with an Organotechnetium Complex, Cancer Research 1993, 53:977-984.

Ross M et al., Lipophilic Triphenylphosphonium Cations as Tools in Mitochondrial Bioenergetics and Fee Radical Biology, Biochemistry (Moscow) 2005, 70:222-230.

Sampalis F et al., International Prospective Evaluation of Scintimammography with 99mTechnetium Sestamibi, Am J of Surg 2003, 185:544-549.

Sheu S et al., Targeting Antioxidants to Mitochondria: A New Therapeutic Direction, Biochim Biophys Acta 2006, 1762:256-265.

Smith R et al., Targeting Coenzyme Q Derivatives to Mitochondria, Meth Enzymol 2004, 382:45-67.

Spanu A et al, The Role of Planar Scintimammography With High-Resolution Dedicated Breast Camera in the Diagnosis of Primary Breast Cancer, Clin Nucl Med 2008, 33(11):739-742).

Spanu A et al., 99mTc-tetrofosmin SPET in the Detection of Both Primary Breast Cancer and Auxiliary Lymph Node Metastasis, Euro J of Nucl Med 2001, 28(12):1781-1794.

Thompson H et al., Rat Models of Premalignant Breast Disease, J of Mamm Gland Biol Neoplas 2000, 5(4):409-420.

Wang et al., 64 Cu-Labeled Triphenylphosphonium and Triphenylarsonium Cations as Highly Tumor-Selective Imaging Agents, J Med Chem 2007, 50:5057-5069.

Dhanasekaran, A., Mitochondria Superoxide Dismutase Mimetic Inhibits Peroxide-Induced Oxidative Damage and Apoptosis: Role of Mitochondrial Superoxide, Free Radic. Biol. Med. 2005, 39(5):567-583.

Hande, K., Clinical Applications of Anticancer Drugs Targeted to Topoisomerase II, Biochimica et Biophysica Acta 1998, 1400:173-184.

Matsumoto, K., et al., High-Resolution Mapping of Tumor Redox Status by Magnetic Resonance Imaging Using Nitroxides as Redox-Sensitive Contrast Agents, Clin. Cancer Res. 2006, 12(8):2455-2462.

Prah, D., et al., In Vivo Mitochondrial Labeling Using Mito-Carboxy Proxyl (Mito-CP) Enhanced Magnetic Resonance Imaging, Proc. Intl. Soc. Mag. Reson. Med. 2007, 15.

Prah, D., et al., In Vivo Mitochondrial Labeling Using Mito-Carboxy Proxyl (Mito-CP) Enhanced Magnetic Resonance Imaging, Proc. Intl. Soc. Mag. Reson. Med. 2008, 16.

Smith, R., et al., Using Mitochondria-Targeted Molecules to Study Mitochondrial Radical Production and Its Consequences, Biochemical Society Transactions 2003, 31(6):1295-1299.

Sugiyama, S., Approaches that Mitigate Doxorubicin-Induced Delayed Adverse Effects on Mitochondrial Function in Rat Hearts; Liposome-Encapsulated Doxorubicin or Combination Therapy with Antioxidant, Biochemistry and Molecular Biology International 1995, 36(5):1001-1007.

Szewczyk, A., et al., Mitochondria as a Pharmacological Target, Pharmacol. Rev. 2002, 54:101-127.

United States Patent and Trademark Office, Office Action Summary and Detailed Action, U.S. Appl. No. 11/834,799, Apr. 29, 2010.

Applicants, Response to Election of Species Requirement, U.S. Appl. No. 11/834,799, May 11, 2010.

United States Patent and Trademark Office, Office Action Summary and Detailed Action, U.S. Appl. No. 11/834,799, Jun. 23, 2010.

Applicants, Response to Non-Final Office Action, U.S. Appl. No. 11/834,799, Oct. 25, 2010.

United States Patent and Trademark Office, Office Action Summary and Detailed Action, U.S. Appl. No. 11/834,799, Dec. 23, 2010.

Wang, et al., Doxorubicin Induces Apoptosis in Normal and Tumor Cells Via Distinctly Different Mechanisms, The Journal of Biological Chemistry, 2004, 279(24)25535-25543.

Yang, et al. Synthesis and Structural Characterization of Complexes of a DO3A-Conjugated Triphenylphosphonium Cation with Diagnostically Important Metal Ions, Inorganic Chemistry, 2007, 46(21):8988-8997.

Applicant, Response to Dec. 23, 2010 Final Office Action and Section 1.132 Declaration, U.S. Appl. No. 11/834,799, Mar. 23, 2011.

United States Patent and Trademark Office, Office Action Summary and Detailed Action, U.S. Appl. No. 11/834,799, Oct. 13, 2011.

United States Patent and Trademark Office, Office Action Summary and Detailed Action, U.S. Appl. No. 12/390,929, Jul. 11, 2011.

Applicant, Response to Jul. 11, 2011 Restriction and Election of Species Requirement, U.S. Appl. No. 12/390,929, Jan. 10, 2012.

United States Patent and Trademark Office, Office Action Summary and Detailed Action, U.S. Appl. No. 12/390,929, Mar. 13, 2012.

Applicant, Response to Mar. 13, 2012 Non-Final Office Action and Declaration Under 37 C.F.R. 1.132, U.S. Appl. No. 12/390,929, Sep. 13, 2012.

* cited by examiner

99M TC-LABELED TRIPHENYLPHOSPHONIUM DERIVATIVE CONTRASTING AGENTS AND MOLECULAR PROBES FOR EARLY DETECTION AND IMAGING OF BREAST TUMORS

CROSS-REFERENCE TO RELATED APPLICATIONS

This application claims priority to and benefit of U.S. Provisional Application Ser. No. 61/032,913, filed on Feb. 29, 2008.

U.S. patent application Ser. No. 12/390,929 filed on Feb. 23, 2009, which is hereby incorporated by reference in its entirety.

STATEMENT REGARDING FEDERALLY SPONSORED RESEARCH

Not applicable.

BACKGROUND OF THE INVENTION

Breast cancer is among the most commonly diagnosed cancers, and it causes the second highest female mortality rate in the United States. (Parker S et al., Cancer Statistics, 1997, *CA Cancer J Clin* 1997, 47:5-27; Jemal, A. et al., Cancer Statistics, 2004, *CA Cancer J Clin* 2004, 54:8-29). Early and accurate diagnosis of breast cancer is critical to successful intervention.

Scintimammography is an adjunct diagnostic tool for patients with suspected breast cancers. (Khalkhali I et al., $^{99m}$Tc Sestamibi Breast Imaging for the Examination of Patients with Dense and Fatty Breasts: Multicenter Study, *Radiology* 2002, 222:149-155; Khalkhali I et al., Scintimammography: The Complementary Role of Tc-99m Sestamibi Prone Breast Imaging for the Diagnosis of Breast Carcinoma, *Radiology* 1995, 196:421-426; Hussain R et al., A meta-analysis of scintimammography: an evidence-based approach to its clinical utility, *Nu Med Comm* 2006, 27:589-594). The technique provides physiological information about the target tissue by utilizing mitochondria-targeting tracers. (Hussain R et al., 2006; Mathieu I et al., Inconclusive Triple Diagnosis in Breast Cancer Imaging: Is There a Place for Scintimammography?, *J Nucl Med* 2005, 46:1574-1581; Liberman M et al., Breast cancer diagnosis by scintimammography: a meta-analysis and review of the literature, *Breast Canc Res Treat* 2003, 80:115-126).

Imaging agents that have been used in scintimammography include $^{99m}$Tc-methoxyisobutylisonitrile ($^{99m}$Tc-MIBI) and $^{99m}$Tc-tetrofosmin. (Sampalis F et al., International prospective evaluation of scintimammography with $^{99m}$Technetium sestamibi, *The Am J of Surg* 2003, 185:544-549; Spanu A et al., $^{99m}$Tc-tetrofosmin SPET in the detection of both primary breast cancer and auxiliary lymph node metastasis, *European J of Nucl Med* 2001, 28(12):1781-1794). Although originally developed as heart imaging agents, the elevated uptake of these mitochondria-targeting agents in carcinomas positively correlates to cancer invasiveness. Elevated uptake is also attributable to active angiogenesis and aberrant oxidative metabolism of tumor cells. (Delmon-Moingeon L et al., Uptake of the Cation Hexakis(2-methoxyisobutylisonitrile)-Technetium-99m by Human Carcinoma Cell Lines in Vitro, *Canc Res* 1990, 50:2198-2202; Papantoniou V et al., The Potential Role of Calcitonin Gene-Related Peptide (CGRP) in Breast Carcinogenesis and Its Correlation With $^{99m}$Tc-(V) DMSA Scintimammography, *Am J of Clinical Oncology* 2007, 30(4)420-427). However, cardiac and hepatic uptake of the existing agents is relatively high in breast imaging, which tends to cause background noise due to close proximity of the heart and liver to mammary tissues.

SUMMARY OF THE INVENTION

One aspect of the invention is a compound according to the structure:

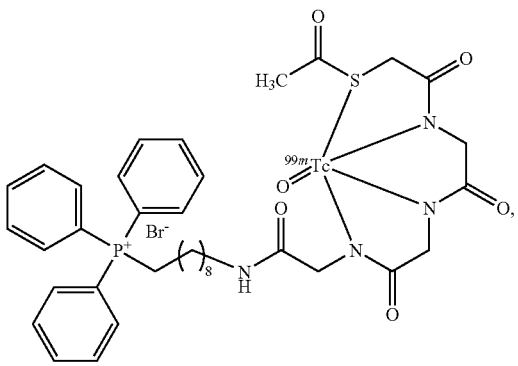

or a solvate or hydrate thereof.

Another aspect of the invention is a compound according to the structure:

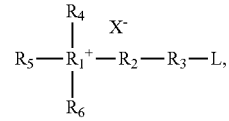

wherein L is $^{99m}$Tc, $^{125}$I, $^{123}$I, $^{123/5/131}$I, $^{18}$F, $^{11}$C, $^{13}$N, $^{15}$O, $^{66/8}$Ga, $^{67}$Ga, $^{60}$Cu, $^{64}$Cu, $^{67}$Cu, $^{52}$Fe, $^{55}$Co, $^{61/2/4}$Cu, $^{62/3}$Zn, $^{70/1/4}$As, $^{75/6}$Br, $^{82}$Rb, $^{86}$Y, $^{89}$Zr, $^{110}$In, $^{111}$In, $^{120/4}$I, $^{201}$Tl or $^{122}$Xe, L being chelated to $R_3$, wherein $R_1$ is S, N or P, wherein $R_2$ is a branched or straight chain, saturated or unsaturated, substituted or unsubstituted $C_{1-25}$ moiety, wherein $R_3$ is a branched or straight chain, cyclic, saturated or unsaturated, substituted or unsubstituted $C_{1-30}$ moiety comprising one or more of carboxyl, amine, amide, ester, alcohol or thiol, wherein $R_4$, $R_5$ or $R_6$ are the same or independently a straight or branched chain, saturated or unsaturated, substituted or unsubstituted $C_{1-10}$ alkyl, substituted or unsubstituted phenyl, or substituted or unsubstituted benzyl, and, wherein $X^-$ is a salt-forming counterion, or a solvate or hydrate thereof.

In an exemplary embodiment of the compound, $X^-$ is $Cl^-$, $I^-$ or $F^-$.

In another exemplary embodiment of the compound, the salt-forming counterion is acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, mitrate, pamoate, pantothenate, phosphate, diphosphate, polygalacturonate, salicylate, stearate, subacetate, succinate, sulfate, tannate, tartrate, teoclate or triethiodide.

In another exemplary embodiment of the compound, $R_2$ is a branched or straight chain, saturated or unsaturated, substituted or unsubstituted $C_{4-10}$ or $C_{4-15}$ alkyl.

In another exemplary embodiment of the compound, L is $^{99m}Tc$.

In another exemplary embodiment of the compound, $R_3$-L is O-(2-$^{18}$F-fluoroethyl)-L-tyrosine, $^{18}$F-fluoromisonidazole, $^{64}$Cu-diacetyl-bis(N-4-methylthiosemicarbazone), 3'-deoxy-3'-($^{18}$F)fluorothymidine ($^{18}$F-FLT), $^{11}$C-thymidine, or $^{18}$F-1-(2'-deoxy-2'-fluoro-β-D-arabinofuranosyl)thymine.

Another aspect of the invention is a process of making the compound according to

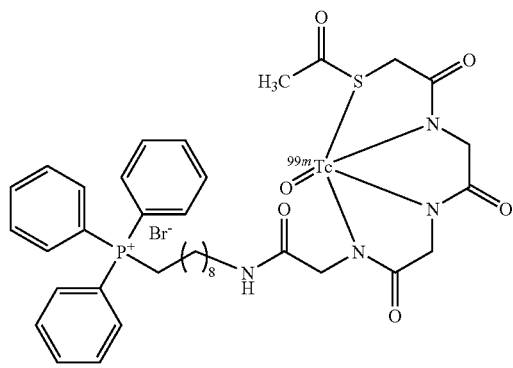

the structure (referred to herein as $^{99m}Tc$-Mito$_{10}$-MAG3), or a solvate or hydrate comprising the steps or acts of providing a compound according to the structure:

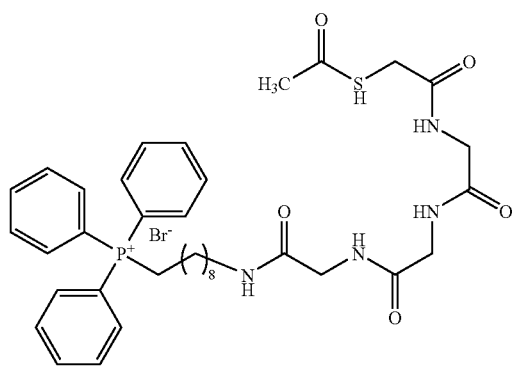

(referred to herein as Mito$_{10}$-MAG3) or a solvate or hydrate thereof, and, radiolabeling the compound by chelating the compound with a radioisotope-containing reactant comprising $^{99m}Tc$.

In an exemplary embodiment of the process, the radioisotope-containing reactant comprises $^{99m}Tc$ pertechnetate.

Another aspect of the invention is an injectable dosage form comprising any of the above compounds and a pharmaceutically suitable injectable carrier system.

Another aspect of the invention is a method of detecting breast cancer in a female human patient in need thereof comprising injecting an injectable dosage form comprising any of the above compounds and a pharmaceutically suitable injectable carrier system, and, scintimammographically imaging the radioactivity of the radioisotope.

The instant compounds may also be referred to as radiopharmaceuticals, imaging agents, molecular probes, radiotracers and the like, and they are used interchangeably.

BRIEF DESCRIPTION OF DRAWINGS OF THE EXEMPLARY EMBODIMENTS

Figure 4:
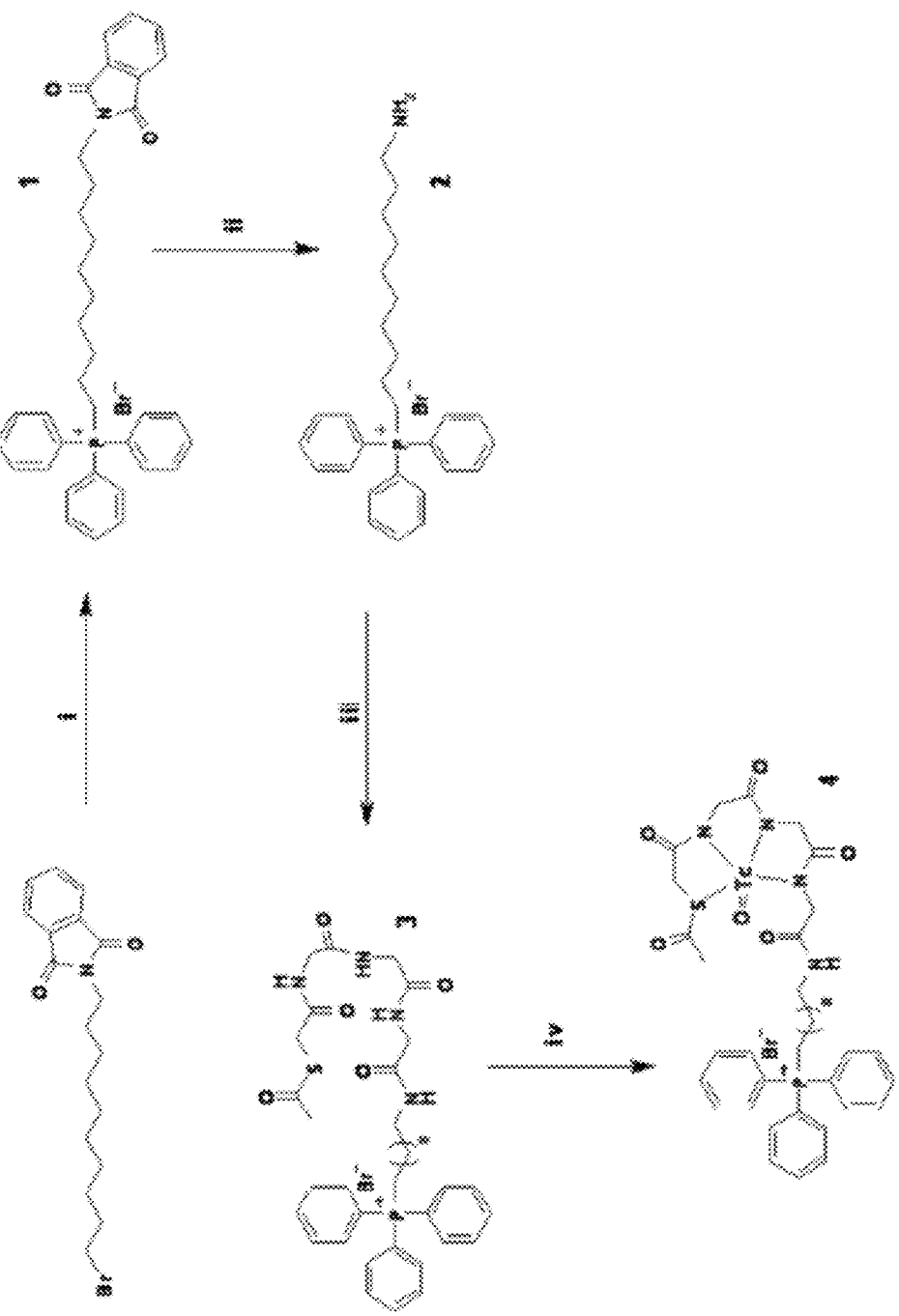

FIG. 4 is a schematic drawing of the chemical synthesis and radiolabeling of Mito$_{10}$-MAG3, whereby (10-phtalimidyl)triphenyl phosphonium bromide [1] was synthesized in reaction (i) from (10-bromodecyl)phthalimide and triphenyl phosphine, whereby (10-aminodecyl)triphenyl phosphonium bromide [2] was synthesized in reaction (ii) using hydrazine, whereby Mito$_{10}$-MAG3 was produced by reaction (iii) involving NHS-MAG3 and (10-aminodecyl)triphenyl phosphonium bromide [3], and, whereby the $^{99m}Tc$-chelated form of Mito$_{10}$-MAG3 is shown [4].

Figure 5:
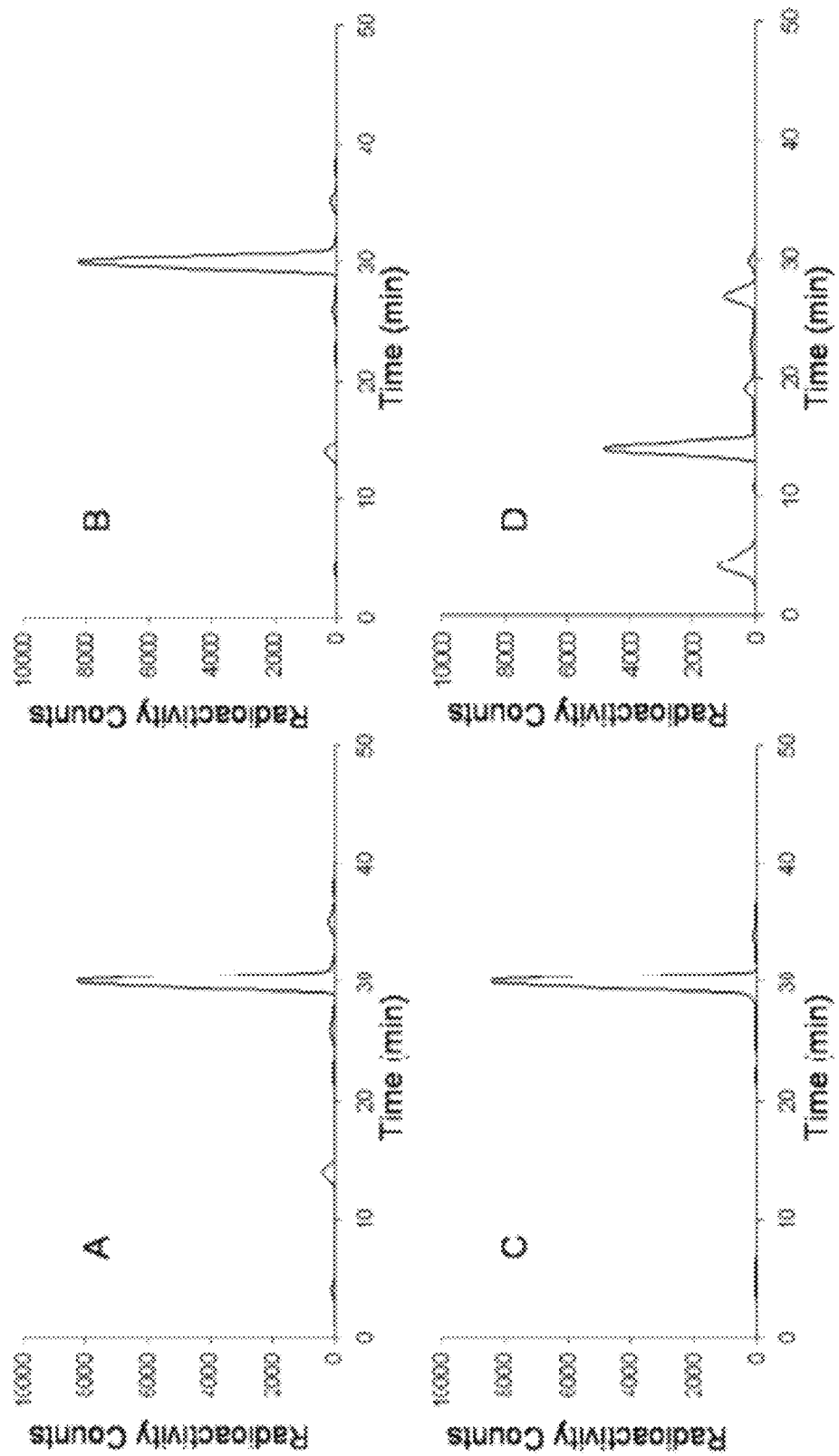

FIG. 5 illustrates the radiochemical stability and pharmacokinetics of $^{99m}Tc$-Mito$_{10}$-MAG3 (Panels A, B and C) as radioHPLC chromatogram of $^{99m}Tc$-Mito$_{10}$-MAG3 at 0, 24 and 48 hr after radiolabeling, whereby no significant change in radiochemical purity is observed, and, whereby Panel D shows radioHPLC chromatogram of a urine sample taken 30 min after the intravenous injection of $^{99m}Tc$-Mito$_{10}$-MAG3, and, whereby the radioactive metabolites are present.

Figure 6:
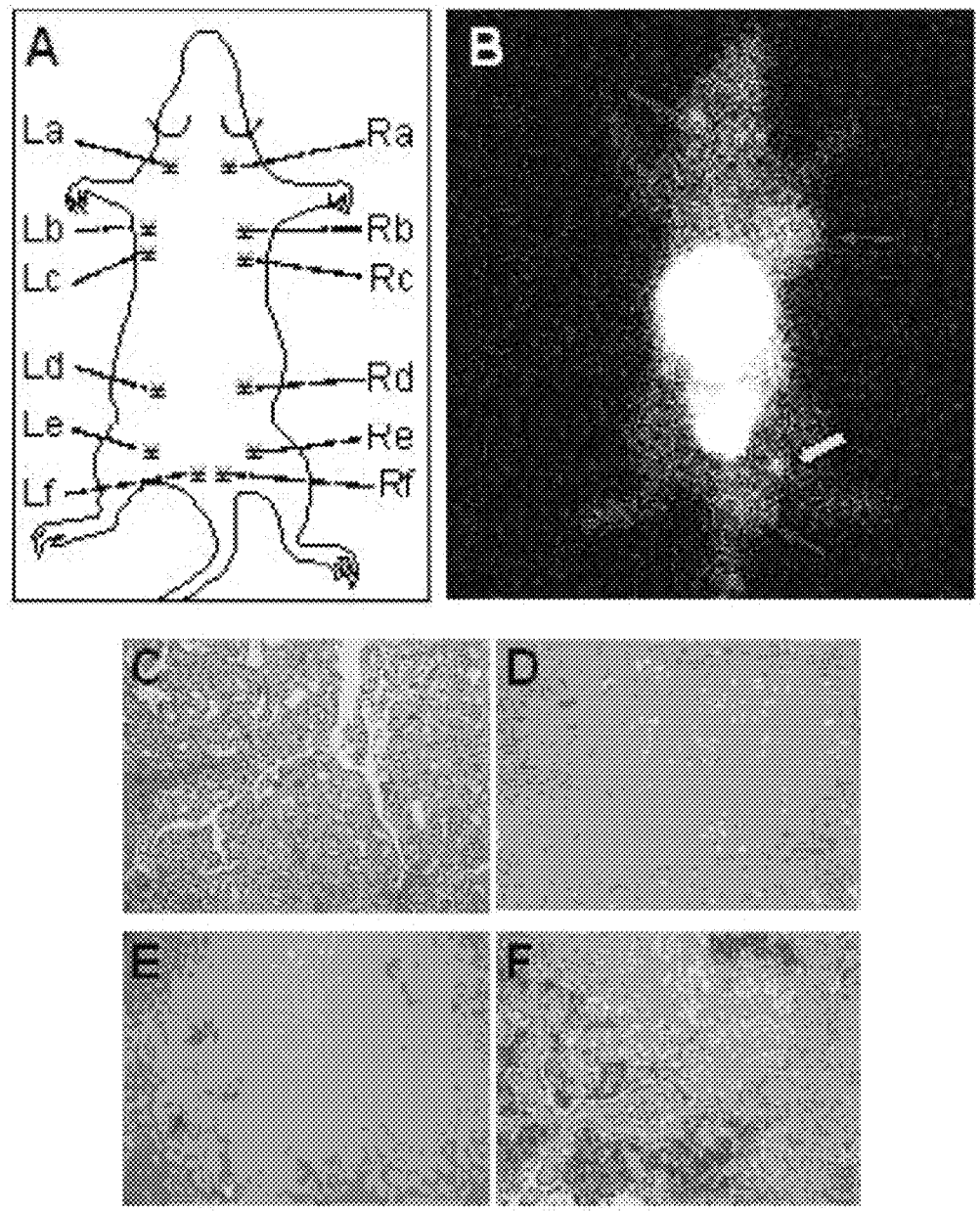

FIG. 6 shows the noninvasive detection of established palpable and non-palpable early growth breast carcinomas in the 7,12-dimethylbenz(a)anthracene (DMBA) induced rat breast cancer model, whereby panel A illustrates the distribution of mammary glands on a female rat, whereby panel B shows an anterior planar image of a tumor-bearing rat acquired after the intravenous injection of $^{99m}Tc$-Mito$_{10}$-MAG3, whereby a suspected, but equivocal, site is marked by a block arrow, whereby panel C shows an early growth breast carcinoma at mammary gland La (confirmed by histology) correlating to a focal radioactivity uptake in the planar image, whereby panel D shows the histology of an established breast tumor at gland Lc, whereby panel E shows the histology of normal mammary tissue harvested from gland Re, and, whereby panel F shows the histology of an established breast carcinoma at gland Rf.

Figure 7:
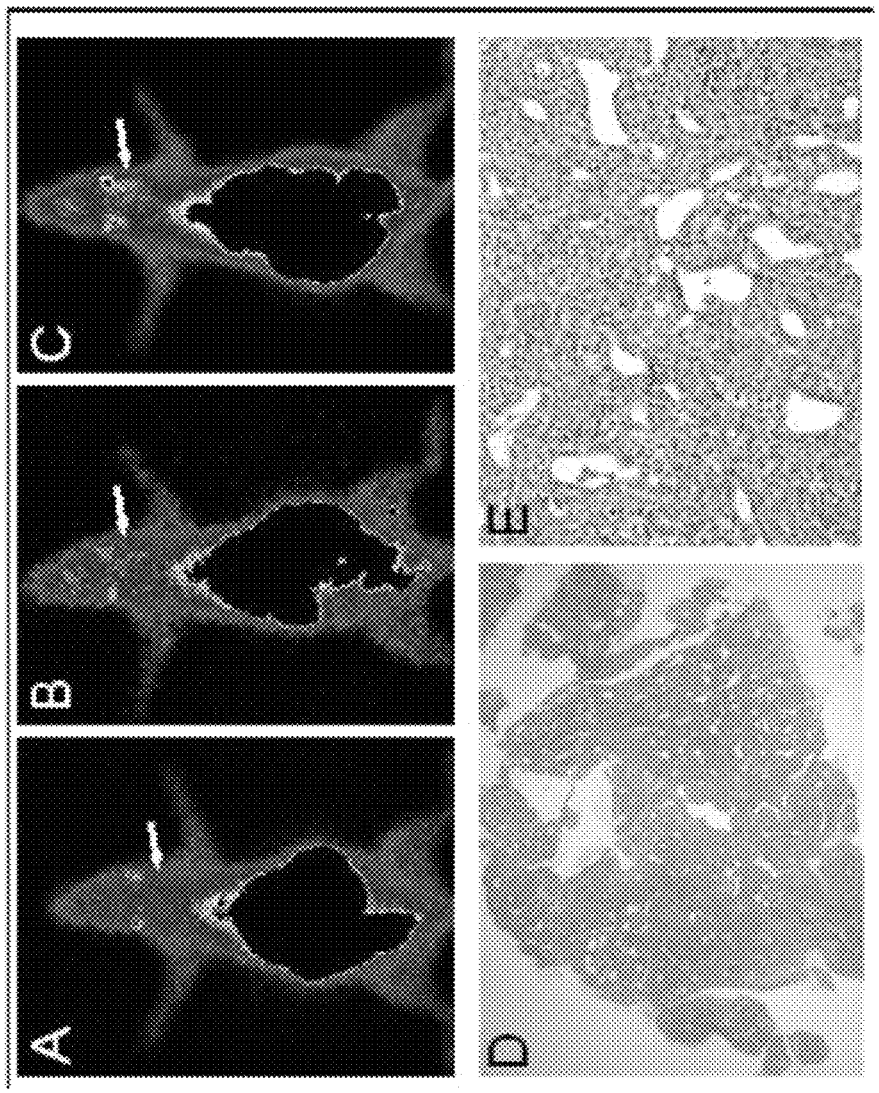

FIG. 7 illustrates an example of the longitudinal study using $^{99m}Tc$-Mito$_{10}$-MAG3 for the early detection of early breast carcinomas in a DMBA-induced rat breast cancer model, whereby anterior images of the same rat from three consecutive weeks are shown in panels A, B and C, whereby the site of progressive tumor growth (as detected by $^{99m}Tc$-Mito$_{10}$-MAG3) is marked by an arrow, and, whereby hematoxylin and eoisin (H&E) stained gross tumor morphology and cellular carcinogenesis of papillary carcinoma are shown in panels D and E, respectively.

Figure 8:
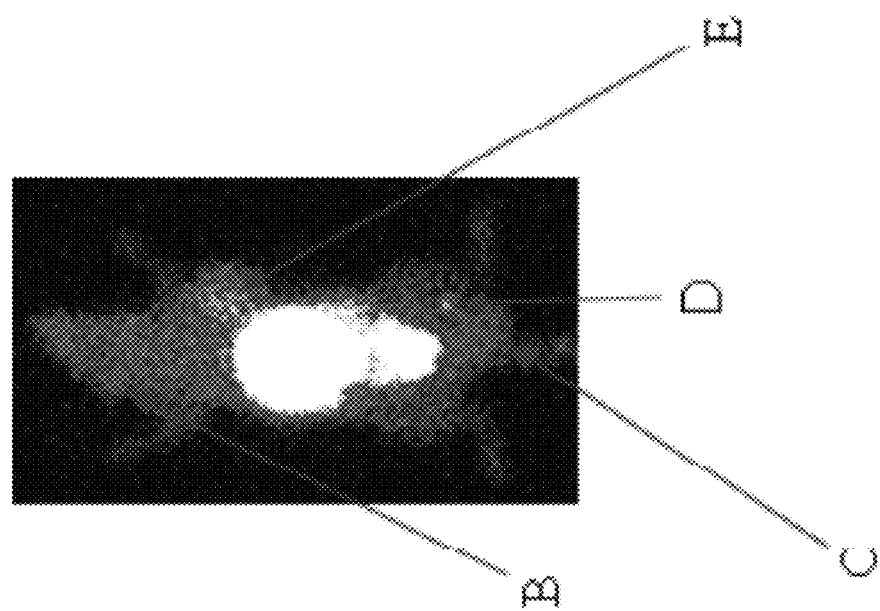

FIG. 8 is an exemplary planar image generated using $^{99m}Tc$-Mito$_{10}$-MAG3.

Figure 9:
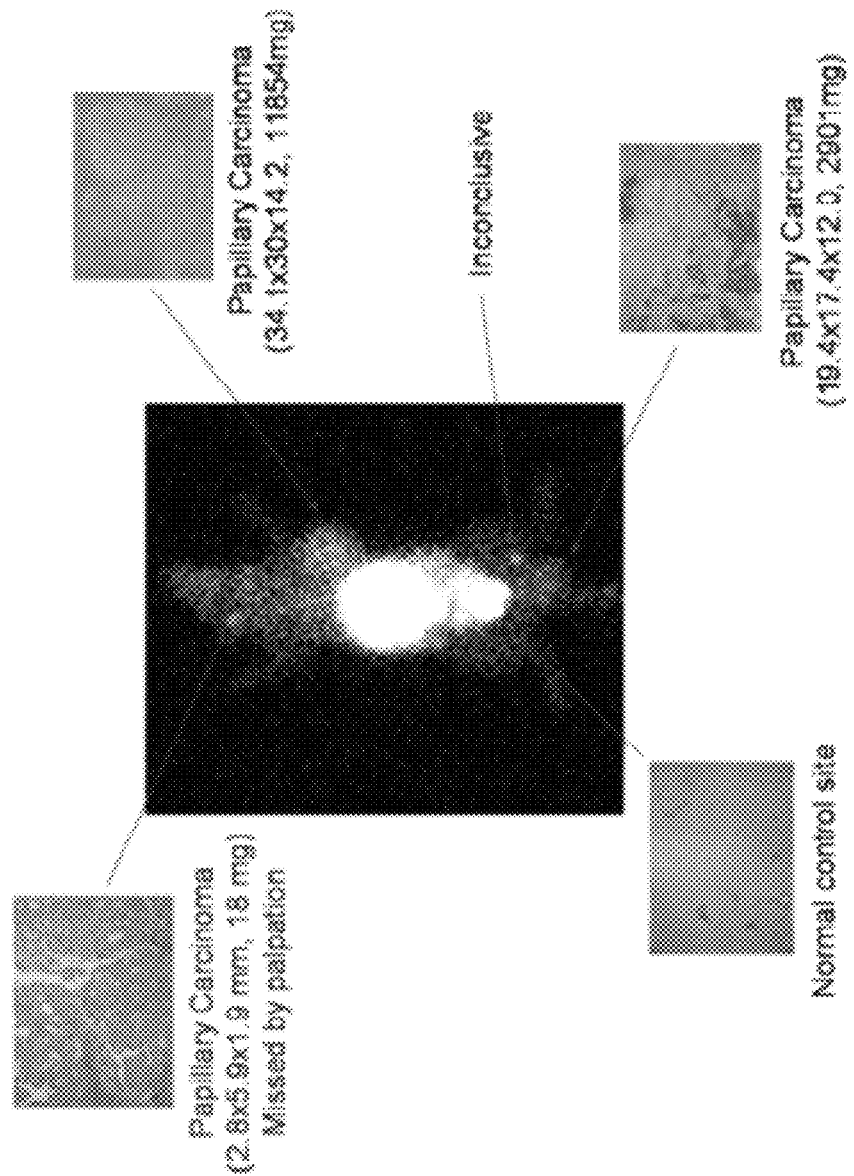

FIG. 9 is an exemplary planar image generated using $^{99m}Tc$-Mito$_{10}$-MAG3 that show small breast tumors missed by palpation examination.

DETAILED DESCRIPTION OF THE EXEMPLARY EMBODIMENTS

Scintimammography has emerged as a promising adjunct imaging modality with improved sensitivity and specificity for detecting breast cancers. The diagnostic value of scintimammography resides in providing a functional assessment of the target tissue using mitochondria-avid imaging agents.

$^{99m}$Tc-Mito$_{10}$-MAG3 possesses advantageous radiopharmaceutical properties. The uptake in the myocardium is reduced by one to two orders of magnitude compared to $^{99m}$Tc-MIBI. $^{99m}$Tc-Mito$_{10}$-MAG3 exhibits fast blood clearance, with a blood half-life of less than 2 min in rats. A diminished myocardial uptake combined with a prompt reduction of cardiovascular blood pool signal to facilitate improved signal-to-background ratios.

In particular, such properties enable detection of lesions in the inferior portions of the mammary tissues in human anatomy that are in close proximity to the heart. Although the initial liver uptake of $^{99m}$Tc-Mito$_{10}$-MAG3 is relatively high, the hepatic signal rapidly declines with time reaching sufficiently low level within 30 min contributing to a low background interference to the thorax. The hepatic background has less influence on breast imaging than that of the heart.

Tumor uptake of $^{99m}$Tc-Mito$_{10}$-MAG3 was followed by a washout suggesting that an active transport mechanism to remove the agent from intracellular compartments. A similar observation has been documented for other cationic lipophilic agents, whereby they are recognized as substrates for P-glycoprotein-dependent efflux. (Piwnica-Worms D et al., Functional Imaging of Multidrug-resistant P-Glycoprotein with an Organotechnetium Complex, *Cancer Research* 1993, 53:977-984; Arbab A et al., Uptake of Technetium-99m-Tetrofosmin, Tecnetium-99m-MIBI and Thallium-201 in Tumor Cell Lines, *J Nucl Med* 1996, 37:1551-1556; Ballinger J, $^{99m}$Tc-Tetrofosmin for Functional Imaging of P-glycoprotein Modulation In Vivo, *J Clin Pharmacol* 2001, 41:39S-47S). The tumor-to-non-tumor ratio for $^{99m}$Tc-Mito$_{10}$-MAG3 was similar to that of $^{99m}$Tc-MIBI in DMBA-induced breast carcinoma in rats. The cardiovascular background of $^{99m}$Tc-Mito$_{10}$-MAG3 is substantially lower, therefore, it provides an improved detection sensitivity in the inferior portions of human mammary tissues.

Importantly, the DMBA-induced breast carcinoma in rats in the in vivo longitudinal experiment set forth herein is a highly relevant disease model in assessing the diagnostic efficacy of novel agents for scintimammography. In this model, the target of action by DMBA is the epithelial cells in the mammary gland. (Thompson H et al., 2000). As in human breast carcinoma, morphologically defined mammary lesions in DMBA-treated rats are initiated from the terminal end buds or terminal ductules. (Thompson H et al., Rat Models of Premalignant Breast Disease, *J of Mammary Gland Biology and Neoplasia* 2000, 5(4):409-420; Foster P et al., A New Therapeutic Strategy against Hormone-Dependent Breast Cancer: The Preclinical Development of a Dual Aromatase and Sulfatase Inhibitor, *Clin Cancer Res* 2008, 14(20):6469-6477). In addition, the ovarian dependency of the rat tumor model adds value to the investigations of hormone-based therapies for breast cancers in humans. (Foster P et al., 2008; Nandi S et al., Hormones and mammary carcinogenesis in mice, rats, and humans: A unifying hypothesis, *Proc Natl Acad Sci USA* 1995, 92:3650-3657). Compared to xenograft tumor models using implanted human cancer cells in rodents, the histogenic characteristics of DMBA-induced lesions in rats better simulates that in the human counterpart, and, thus provides a more realistic testing ground. By assessing the detection of DMBA-induced carcinoma in an early growth phase, important information is provided concerning the diagnostic efficacy of candidate imaging agents for breast cancer.

Apart from $^{99m}$Tc-Mito$_{10}$-MAG3, the imaging properties of triphenyl phosphate (TPP) cation-based derivatives may be modulated by alternative chemical structures. The instant 10-carbon alkyl chain provides synergistic mitochondria-targeting efficiency with minimal membrane toxicity. Other lengths and types of functional groups between the TPP head group and the chelation site of the radioisotope may be used as well. (Asin-Cayuela J et al., Fine-tuning the hydrophobicity of a mitochondria-targeted antioxidant, *FEBS Letters* 2004, 571:9-16). Mito$_{10}$-MAG3, has a 10-carbon alkyl linker. It has been reported that the configuration of the radioligands may substantially alter the biodistribution and pharmacokinetics of radiopharmaceuticals.

SPECT examinations are conducted by injecting a radiopharmaceutical composition (that contains a dilution marker and/or contrast agent) into the body of a patient to be examined. The contrast agent contains an isotope that emits photons at one or more energy level. The isotope accumulates in an organ to be imaged, whereby isotope and radiopharmaceutical concentrations may be substantially limited in the imaged organ.

While moving through a patient's blood stream, the isotope and radiopharmaceutical concentrate in the imaged organ. Organ characteristics (such as irregularities) are identified and assessed by measuring photon intensity emitted from the organ.

Photon intensity is measured at a prescribed time following injection of the radiopharmaceutical. A planar gamma camera is positioned adjacent the relevant portion of the patient's body where the organ to be imaged is located. The camera detects photon emissions and creates a planar view of the organ corresponding to the camera position during the imaging period. The camera is supported in a single position while the patient remains as still as possible.

A gamma camera includes a collimator, a scintillation crystal, and a detector. The collimator typically includes a lead block with tiny holes there through that define preferred photon paths. The preferred paths are usually unidirectional and perpendicular to the length of the collimator. The collimator blocks emissions toward the crystal along non-preferred paths.

The scintillation crystal is positioned adjacent to the collimator on a side opposite the patient. The crystal absorbs photons passing through the collimator on a front surface, and it emits light from a back surface when a photon is absorbed. The detector includes a planar arrangement of photomultiplier tubes (PMTs) positioned adjacent to the crystal and on one side of the crystal opposite the collimator. Light emitted by the crystal is detected by the PMTs that in turn generate analog intensity signals indicating the precise position of emission impact on the crystal.

A processor receives the PMT signals and digitally stores corresponding information as M by N arrays of elements called pixels. The values of M and N are commonly 64 or 128 pixels across each of the two image dimensions. The M and N arrays of pixel information is used by the processor to form an emission image corresponding to the specific camera position.

In addition to the camera and processor, gamma detection systems also include a stand or gantry as well as a patient support table. The stand or gantry supports the camera in one position at a time, adjacent to the relevant portion of the patient, and it can also be used (after generating one image using collected data) to move the camera to a second position respective to the patient to generate a second image.

Most gamma imaging procedures are used to generate tomographic images. Such procedures need a plurality of emission images, whereby each image is generated by positioning the detector parallel to (and at different angles about) an imaging axis.

To shorten the total scan time, two or more separate gamma cameras rotated about the subject may be used to generate various sets of view angles. Where two gamma cameras are employed, the cameras may be positioned in various positions around the subject. For example, the gamma cameras may be positioned on opposite sides of the patient such that 360° of view angles are generated by rotating the gantry through 180°. The gamma cameras may also be positioned at 90° such that 180° of view angles are generated by rotating the gantry through 90°.

$^{99m}$Tc has very favorable radiological properties, such as 140 keV and 6 hr physical half-life. $^{99m}$Tc is also accessible without the requirement for a cyclotron. However, the spatial resolution and sensitivity of clinical gamma cameras and SPECT may still be trailing that of PET scanners. Specialized gamma cameras dedicated to scintimammography with smaller field-of-views and greater spatial resolution have been recently developed. Using these gamma cameras, improved diagnostic performances were demonstrated in clinical trials. (Brem R et al., Occult Breast Cancer: Scintimammography with High-Resolution Breast-specific Gamma Camera in Women at High Risk for Breast Cancer, *Radiology* 2005, 237:274-280; Brem R et al., Breast-specific Gamma Imaging as an Adjunct Imaging Modality for the Diagnosis of Breast Cancer, *Radiology* 2008, 247(3):651-657; Brem R et al., High-Resolution Scintimammography: A Pilot Study, *J Nucl Med* 2002, 43:909-915; Spanu A et al, The Role of Planar Scintimammography With High-Resolution Dedicated Breast Camera in the Diagnosis of Primary Breast Cancer, *Clin Nucl Med* 2008, 33(11):739-742). The technical drive for optimized imaging probes and improved detection modules may eventually lead to better clinical performances.

The synthesis and characterization of the instant TPP cation-based mitochondria-targeting agent, $^{99m}$Tc-Mito$_{10}$-MAG3, is useful for scintimammography. $^{99m}$Tc-Mito$_{10}$-MAG3 has substantially lower cardiac uptake and maintains tumor-avid binding activity in the DMBA-induced rat model of breast carcinoma. Imaging with $^{99m}$Tc-Mito$_{10}$-MAG3 also synergistically provided superior detection of early breast tumors in a relevant animal model. Thus, TPP cation-based radiopharmaceuticals (such as $^{99m}$Tc-Mito$_{10}$-MAG3) are advantageous imaging agents for scintimammography.

The invention covers the synthesis and use of $^{99m}$Tc-labeled alkyl triphenylphosphonium (Mito), via a mercaptoacetyltriglycerine (MAG3) chelating core, in radio-imaging applications. The invention also covers mitochondria targeted molecular imaging and contrast agent compounds that are relevant in cancer biology and medicine. The invention covers synthesizing and applying mitochondria targeted molecular imaging and contrast agent compound in tumor diagnosis and therapy.

A greater mitochondrial membrane potential in tumor cells has been shown to enhance the accumulation of TPP derivatives. One aspect of the invention is synthesis and characterization of $^{99m}$Tc-labeled alkyl TPP ($^{99m}$Tc-Mito$_{10}$-MAG3) for the early detection of breast tumors.

The instant invention includes a TPP cation-based mitochondria imaging agent for the early detection of breast tumors. The membrane potential from outside the cell to mitochondria from tumor cells is at least 60 mV greater (more negative) than in the mitochondria from normal cells. (Kroemer G, Mitochondria in Cancer, *Oncogene* 2006, 25:4630-4632; Ross M et al., Lipophilic Triphenylphosphonium Cations as Tools in Mitochondrial Bioenergetics and Fee Radical Biology, *Biochemistry (Moscow)* 2005, 70:222-230). Consequently, because of their membrane potential-dependent uptake activity, TPP derivatives accumulate approximately 10-fold higher in tumor cell mitochondria. (Ross M et al., 2005; Cooper W et al., $^1$H NMR Visible Lipids Are Induced by Phosphonium Salts and 5-Fluorouracil in Human Breast Cancer Cells, *Magnetic Resonance in Med* 2001, 45: 1001-1010; Smith R et al., Targeting coenzyme Q Derivatives to Mitochondria, *Methods in Enzymology* 2004, 382:45-67; Sheu S et al., Targeting antioxidants to mitochondria: A new therapeutic direction, *Biochinica et Biophysica Acta* 2006, 1762:256-265). As established mitochondria-targeting vectors, the TPP compounds are attractive alternatives to the existing imaging agents.

Set forth herein is the synthesis and characterization of a $^{99m}$Tc-labeled TPP derivative, Mito$_{10}$-MAG3. The compound consists of a TPP head group as the targeting vector, a 10-carbon alkyl linker, and, a MAG3 group as the chelation site for $^{99m}$Tc. The use of $^{99m}$Tc-Mito$_{10}$-MAG3 enabled the detection of small breast tumors on the mg level in a rat model of chemically induced breast carcinomas. $^{99m}$Tc-Mito$_{10}$-MAG3 also significantly reduced cardiac uptake compared with $^{99m}$Tc-MIBI. These results demonstrate that $^{99m}$Tc-Mito$_{10}$-MAG3 is superior to existing scintimammography imaging agents.

Figure 1:
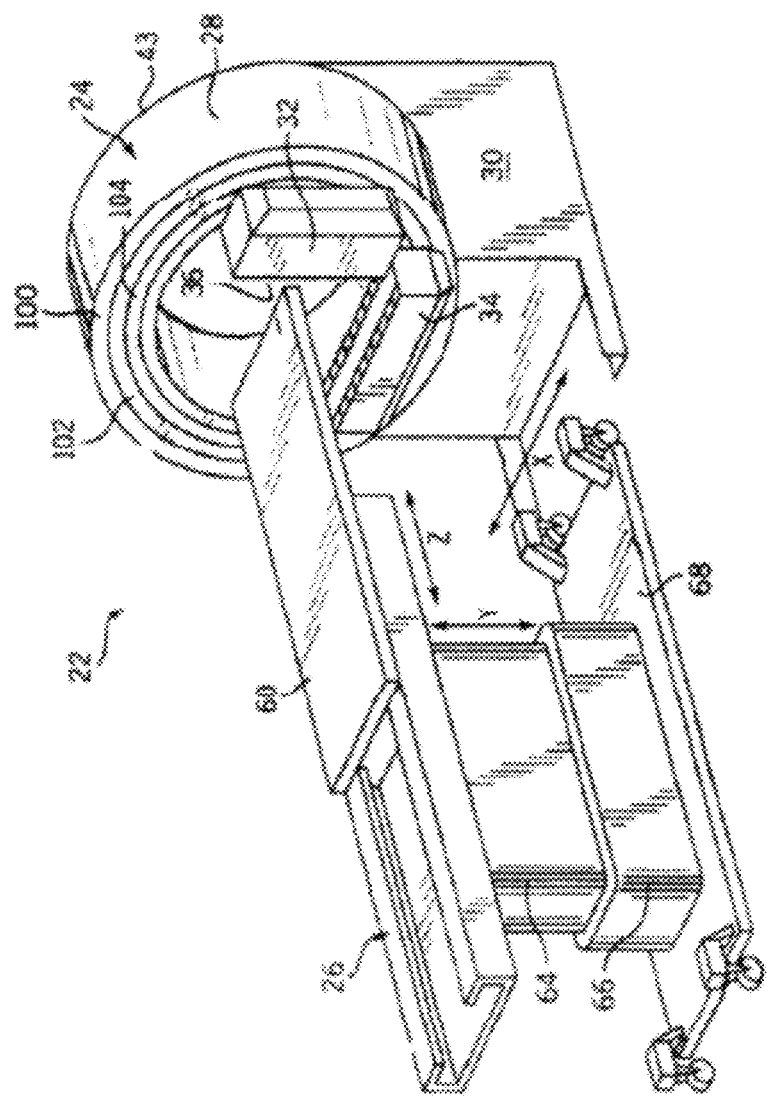
FIG. 1 is a pictorial view of an exemplary single photon emission computed tomography (SPECT) system.

The instant contrast agents may be designed for use with imaging modalities such as SPECT and PET. Referring to FIG. 1, there is shown, generally at 22, an imaging system including a tomography machine 24 and a patient support table 26. Table 26 includes a top surface 60 which allows supported movement of the top surface 60 along a scanning or horizontal Z-axis. The top surface 60 is supported by a vertical leg 64 which extends upwardly from a collar 66. The length of leg 64 can be increased or decreased to raise or lower top surface 60 along a vertical Y-axis. Collar 66 is secured to a dolly 68 having four wheels. Thus, the table 26 enables an operator to position a subject on the top surface 60 in the bore of the tomographic machine 24.

The tomography machine 24 includes a pedestal 30, a gantry 28 and two planar gamma cameras 32, 34. The top surface of the pedestal 30 receives an outer surface of gantry 28 and it houses a motor for rotating moving components of the gantry 28 about a central gantry rotation axis 36 as described in more detail below. The gantry 28 includes an annular race housing 100, which encircles first and second moveable rings 102, 104. Each of the rings 102 and 104 is annular shaped and when the machine 24 is assembled, all of the rings are concentric about the imaging axis 36.

The gamma cameras 32 and 34 are each attached to one of the movable rings 102 and 104. The rings 102 and 104 may be unlocked from each other and rotated on their separate rings 102 and 104 to a number of different configurations. For example, they may be oriented 180° apart for one scan and they may be oriented 90° apart for another scan. The rings 102 and 104 are then locked together and rotated in unison during the scan to rotate both cameras about the subject through the prescribed range of view angles.

Figure 2:
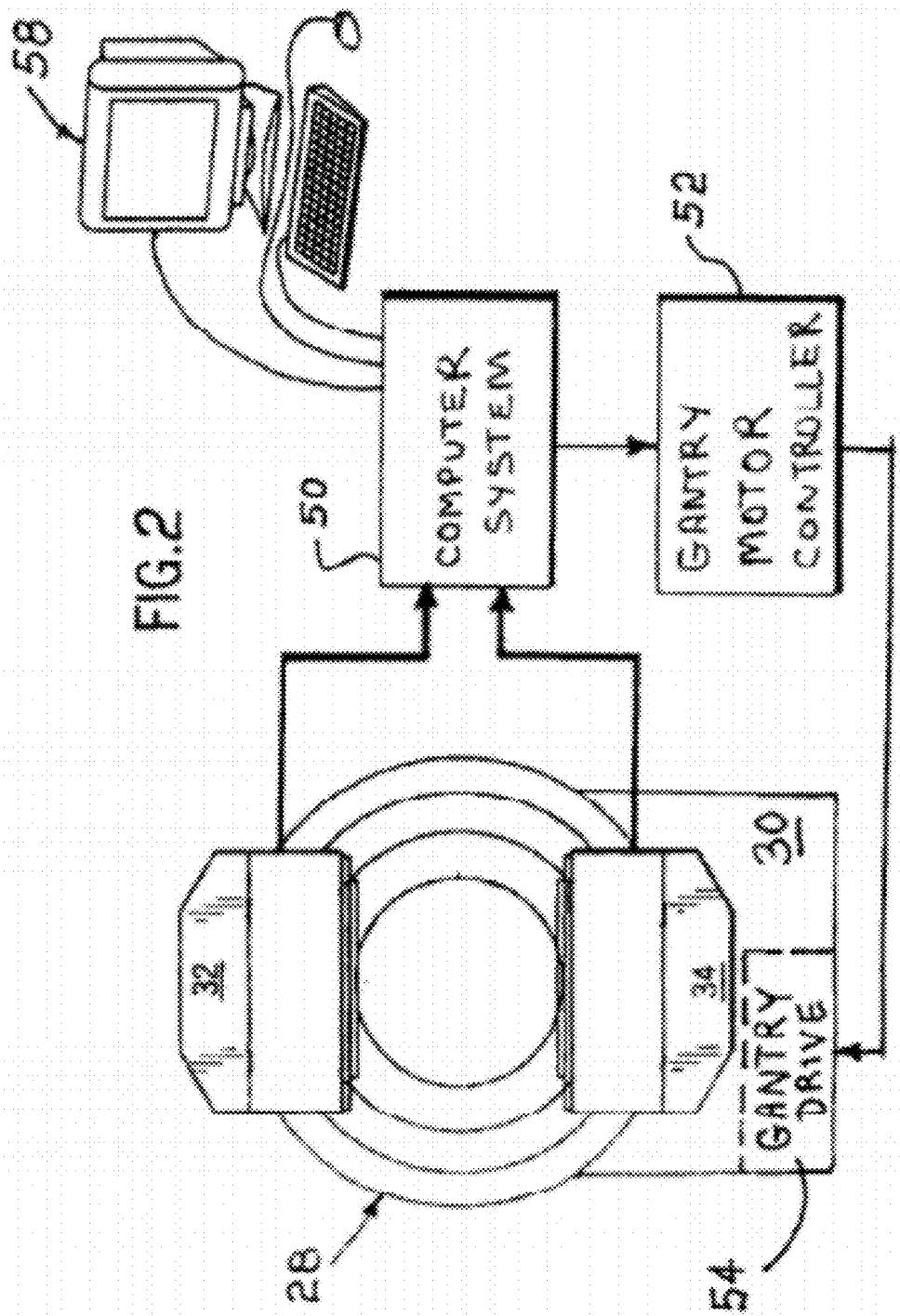
FIG. 2 is a block diagram of the SPECT system of FIG. 1.

Referring particularly to FIG. 2, the gamma cameras 32 and 34 detect and identify coordinates of gamma emissions from a subject being examined. Each camera 32, 34 includes a lead plate that defines a myriad of fine holes perpendicular to its length so that the plate acts as a collimator defining parallel paths there through. A scintillation crystal is positioned behind each collimator which absorbs gamma emissions which pass through the collimator holes perpendicular to its length and produce light emissions corresponding to each absorbed gamma emission. The light emissions are directed toward an array of closely packed PMTs. Detected light emissions cause the PMTs to produce analog signals which are sent to a computer system that uses the signals to compute M and N coordinates of each gamma emission absorbed in terms of analog signal magnitudes.

Computing the M and N coordinates in terms of analog signals is well known. One scheme for determining the M and N coordinates of each gamma emission is described in U.S. Pat. No. 4,142,102 which is incorporated herein by reference. The analog M and N coordinate signals are then used by the computer system 50 to generate an emission image corresponding to the collected data. One scheme for generating emission images is described in U.S. Pat. No. 5,337,231 which is incorporated herein by reference.

The computer system 50 controls the rotation of the gantry 28 by issuing motion commands to a gantry motor controller 52. The gantry motor controller 52 in turn operates a gantry drive 54 located in the gantry 28 to rotate the gamma cameras 32 and 34 around the subject during an emission scan.

The computer system 50 receives commands and scanning parameters from an operator via a console 58 that has a keyboard and display. The operator may observe the reconstructed image and other data from the computer system 50 and the operator may enter commands that prescribe the emission scan that is to be performed.

Figure 3:
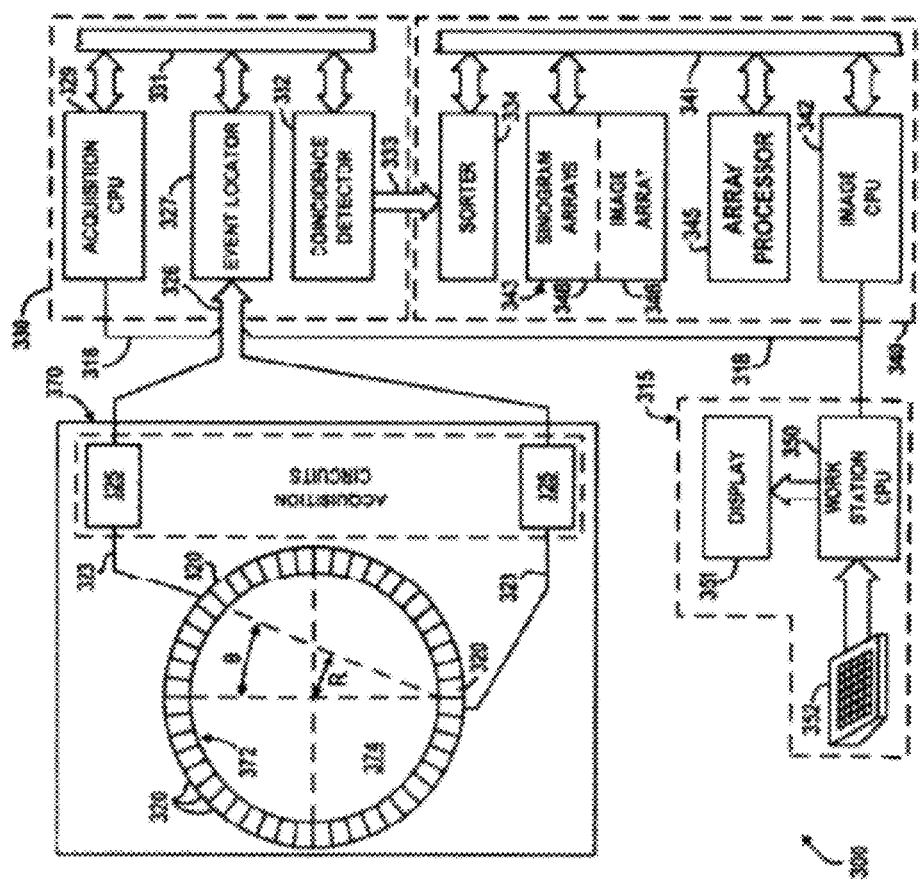
FIG. 3 is a schematic diagram of a photon emission tomogrpahy (PET) imaging system.

Referring now to FIG. 3, a PET system 300 includes a plurality of PET detector rings 372 which are supported by a cylindrical PET gantry 370. The detector ring 372 is comprised of detector units 320. The signals produced by the detector units 320 are then received by a set of acquisition circuits 325 that produce digital signals indicating the event coordinates (x, y) and the total energy. These signals are sent through a cable 326 to an event locator circuit 327 housed in a separate cabinet. Each acquisition circuit 325 also produces an event detection pulse (EDP) which indicates the exact moment the scintillation event took place.

The event locator circuits 327 form part of a data acquisition processor 330 which periodically samples the signals produced by the acquisition circuits 325. The processor 330 has an acquisition CPU 329 which controls communications on local area network 318 and a backplane bus 331. The event locator circuits 327 assemble the information regarding each valid event into a set of digital numbers that indicate precisely when the event took place and the position of the scintillator crystal which detected the event. This event data packet is conveyed to a coincidence detector 332 which is also part of the data acquisition processor 330.

The coincidence detector 332 accepts the event data packets from the event locators 327 and determines if any two of them are in coincidence. Coincidence is determined by a number of factors. Events which cannot be paired are discarded, but coincident event pairs are located and recorded as a coincidence data packet. Each coincidence data packet is a data stream which includes a pair of digital numbers that precisely identify the location of the two detector modules that detect the event.

The coincidence data packets are conveyed through a link 333 to a sorter 334. The sorter 334 forms part of an image reconstruction processor 340. The sorter 334 counts all events occurring along each projection ray (R, θ) and organize them into a two dimensional sinogram array 348 which is stored in a memory module 343. In other words, a count at sinogram location (R, θ) is increased each time a corrected coincidence data packet at that projection ray is received. The image reconstruction processor 340 also includes an image CPU 342 that controls a backplane bus 341 and links it to the local area network 318. An array processor 345 also connects to the backplane 341 and it reconstructs an image from the sinogram array 348. The resulting image array 346 is stored in memory module 343 and is output by the image CPU 342 to the operator work station 315.

The operator work station 315 includes a CPU 350, a display 351 and a keyboard 352. The CPU 350 connects to the local area network 318 and it scans the keyboard 352 for input information. Through the keyboard 352 and associated control panel switches, the operator can control the calibration of the PET scanner and its configuration. Similarly, the operator can control the display of the resulting image on the display 351 and perform image enhancement functions using programs executed by the work station CPU 350.

The instant invention includes a system and method that provides greater specificity than a mammogram, which is especially poor when applied to dense tissues. The instant system also provides higher sensitivity than optical imaging, palpation, and ultrasound. The instant contrast agents have an advantageous physical half-life (6 hr), which is unexpectedly superior to other radioisotopes. $^{99m}Tc$-Mito$_{10}$-MAG3 also has a fast clearance from the circulatory system and provides a low background in the thoracic region. $^{99m}Tc$-Mito$_{10}$-MAG3 may also be administered at a low injection dose yielding less/improved toxicity, immunogenicity and clearance.

Contrast agents and radiopharmaceuticals of the instant invention are defined in accordance with the following structure:

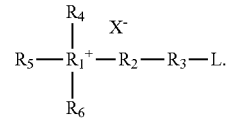

$R_1$ may be S, N or P. $R_2$ may be a branched or straight chain, saturated or unsaturated, substituted or unsubstituted $C_{1-25}$ group. $R_3$ may be a branched or straight chain, cyclic, saturated or unsaturated, substituted or unsubstituted $C_{1-30}$ moiety containing one or more of carboxyl, ester, alcohol, thiol, amide or amine. $R_4$, $R_5$ or $R_6$ are the same or independently a straight or branched chain, saturated or unsaturated, substituted or unsubstituted $C_{1-10}$ alkyl, substituted or unsubstituted phenyl, or substituted or unsubstituted benzyl. $X^-$ is $Cl^-$, $I^-$, $Fl^-$ or another salt-forming counterion.

In an exemplary embodiment, $R_4$, $R_5$ or $R_6$ may be methyl, ethyl, propyl, isopropyl, butyl or isobutyl groups. In another exemplary embodiment, $R_1$, $R_4$, $R_5$ and/or $R_6$ may be substituted by a pyridinium moiety.

$X^-$ is the counterion of the cationic moiety. $X^-$ may be a halogen or an organic salt such as citrate or succinate. The particular salt employed may affect the solubility of the contrasting agent compound.

In an exemplary embodiment, $R_2$ is a straight or branched chain $C_{4-10}$ or $C_{4-15}$ alkyl group. Importantly, $R_2$ affects the hydrophobicity of the compound, which in turn affects it's uptake in the mitochondria.

$R_3$ is a functional group that links the targeting moiety with the radiolabeled moiety, such as amine, carboxyl, ester, alcohol or thiol.

L is the chelating moiety that contains the radionucleotide. It may be several different moieties since they vary depending on the radiolabel used in the molecule. For $^{99m}Tc$, $^{125}I$ and $^{123}I$, exemplary chelating moieties include MAG3, hydrazinonicotinae (HYNIC) and tyrosine.

The radionucleotide may depend upon the imaging modality being employed. For PET, the following radioisotopes may be advantageously used: $^{11}C$, $^{13}N$, $^{15}O$, $^{66/8}Ga$, $^{60}Cu$, $^{52}$Fe, $^{55}$Co, $^{61/2/4}$Cu, $^{62/3}$Zn, $^{70/1/4}$As, $^{75/6}$Br, $^{82}$Rb, $^{86}$Y, $^{89}$Zr, $^{110}$In, $^{120/4}$I, $^{122}$Xe. $^{18}$F based tracers like O-(2-$^{18}$F-fluoroethyl)-L-tyrosine ($^{18}$F-FET)(amino acids); $^{18}$F-fluoromisonidazole ($^{18}$F-FMISO), $^{64}$Cu-diacetyl-bis(N4-methylthiosemicarbazone) ($^{64}$Cu-ATSM (hypoxia)), 3'-deoxy-3'-($^{18}$F) fluorothymidine ($^{18}$F-FLT), $^{11}$C-hymidine, or, $^{18}$F-1-(2'-deoxy-2'-fluoro-β-D-arabinofuranosyl)thymine ($^{18}$F-FMAU) may also be used. For SPECT, the following radioisotopes may be advantageously used $^{99m}$Tc, $^{123/5/131}$I, $^{67}$Cu, $^{67}$Ga, $^{111}$In or $^{201}$Tl.

Another example is shown below.

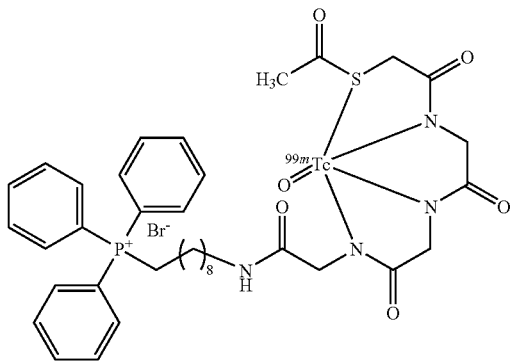

Alkyl phosphonium cations are established agents that target functional mitochondria. The triphenyl moiety directs the contrasting agent to the mitochondria. The positively-charged moiety penetrates the mitochondrial membrane due (at least in part) to the negative potential inside the mitochondrion. The number of carbons in the spacer moiety (i.e., $R_2$) affects the hydrophobicity of the agent, which in turn affects membrane permeability.

It is well recognized in the art that the technology of contrasting agents (and their usefulness for imaging various body tissue) is highly unpredictable. The instant contrast agents and their method of use are unexpectedly superior and synergistic as compared to other known contrasting agents. The instant contrast agents provided unpredictably improved radiochemistry, pharmacokinetics, biodistribution, and, tumor uptake kinetics, particularly as compared to $^{64}$Cu-labeled TPP based contrast agents used in PET and $^{99m}$Tc-MIBI.

As used herein, a salt-forming counterion may be a pharmaceutically suitable (i.e., pharmaceutically acceptable) salt including, but not limited to, acid addition salts formed by mixing a solution of the instant compound with a solution of a pharmaceutically acceptable acid. The pharmaceutically acceptable acid may be hydrochloric acid, methanesulphonic acid, fumaric acid, maleic acid, succinic acid, acetic acid, benzoic acid, oxalic acid, citric acid, tartaric acid, carbonic acid or phosphoric acid. Various pharmaceutically acceptable salts are well known in the art and may be used with the instant compound such as those disclosed in Berge S M et al., "Pharmaceutical Salts." J. Pharm. Sci. 66:1-19 (1977) and Haynes D A et al., "Occurrence of pharmaceutically acceptable anions and cations in the Cambridge Structural Database," J. Pharm. Sci. 94:2111-2120 (2005), which are hereby incorporated herein by reference. For example, the list of FDA-approved commercially marketed salts includes acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glucepate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, mitrate, pamoate, pantothenate, phosphate, diphosphate, polygalacturonate, salicylate, stearate, subacetate, succinate, sulfate, tannate, tartrate, teoclate, and triethiodide. The salt-forming counterion may also be Cl$^-$, I$^-$ or F$^-$.

As used herein, "hydrates" of the instant compound may be a pharmaceutically suitable (i.e., pharmaceutically acceptable) hydrate that is a compound formed by the addition of water or its elements to a host molecule (e.g., the free form version of the compound) including, but not limited to, monohydrates, dihydrates, etc.

As used herein, "solvates" of the instant compound may be a pharmaceutically suitable (i.e., pharmaceutically acceptable) solvate, whereby solvation is an interaction of a solute with the solvent which leads to stabilization of the solute species in the solution, and whereby the solvated state is an ion in a solution complexed by solvent molecules. Solvates and hydrates may also be referred to as "analogues."

As used herein, the injectable and infusion dosage forms (i.e., parenteral dosage forms) include, but are not limited to, liposomal injectables or a lipid bilayer vesicle having phospholipids that encapsulate an active drug substance. Injection includes a sterile preparation intended for parenteral use.

Five distinct classes of injections exist as defined by the USP: emulsions, lipids, powders, solutions and suspensions. Emulsion injection includes an emulsion comprising a sterile, pyrogen-free preparation intended to be administered parenterally. Lipid complex and powder for solution injection are sterile preparations intended for reconstitution to form a solution for parenteral use. Powder for suspension injection is a sterile preparation intended for reconstitution to form a suspension for parenteral use. Powder lyophilized for liposomal suspension injection is a sterile freeze dried preparation intended for reconstitution for parenteral use that is formulated in a manner allowing incorporation of liposomes, such as a lipid bilayer vesicle having phospholipids used to encapsulate an active drug substance within a lipid bilayer or in an aqueous space, whereby the formulation may be formed upon reconstitution. Powder lyophilized for solution injection is a dosage form intended for the solution prepared by lyophilization ("freeze drying"), whereby the process involves removing water from products in a frozen state at extremely low pressures, and whereby subsequent addition of liquid creates a solution that conforms in all respects to the requirements for injections. Powder lyophilized for suspension injection is a liquid preparation intended for parenteral use that contains solids suspended in a suitable fluid medium, and it conforms in all respects to the requirements for Sterile Suspensions, whereby the medicinal agents intended for the suspension are prepared by lyophilization. Solution injection involves a liquid preparation containing one or more drug substances dissolved in a suitable solvent or mixture of mutually miscible solvents that is suitable for injection. Solution concentrate injection involves a sterile preparation for parenteral use that, upon addition of suitable solvents, yields a solution conforming in all respects to the requirements for injections. Suspension injection involves a liquid preparation (suitable for injection) containing solid particles dispersed throughout a liquid phase, whereby the particles are insoluble, and whereby an oil phase is dispersed throughout an aqueous phase or vice-versa. Suspension liposomal injection is a liquid preparation (suitable for injection) having an oil phase dispersed throughout an aqueous phase in such a manner that liposomes (a lipid bilayer vesicle usually containing phospholipids used to encapsulate an active drug substance either within a lipid bilayer or in an aqueous space) are formed. Suspension sonicated injection is a liquid preparation (suitable for injection) containing solid particles dispersed throughout a liquid phase, whereby the particles are insoluble. In addition, the product may be sonicated as a gas is bubbled through the suspension resulting in the formation of microspheres by the solid particles.

The parenteral carrier system includes one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives.

EXAMPLES

Example 1

Synthesis and characterization of $^{99m}$Tc-labeled alkyl triphenylphosphonium (Mito), via the mercaptoacetyltriglycerine (MAG3) chelating core.

Methods. Mito-MAG3 was synthesized by coupling (10-aminodecyl)triphenylphosphonium bromide with NHS-MAG3. Mito-MAG3 was labeled with $^{99m}$Tc according to an existing protocol. Breast tumors were induced in female Sprague Dawley rats using DMBA treatment. $^{99m}$Tc-Mito-MAG3 (15 μg) was injected via the tail vein. Whole body anterior dynamic images were captured on a gamma camera. Tumor tissues were dissected after imaging, and confirmed by histology.

Results. The molecular weight of Mito-MAG3 was confirmed using mass spectrometry. The radiochemical purity of $^{99m}$Tc-Mito-MAG3 determined by reversed phase radio-HPLC was typically greater than 92%. Once injected i.v., the radiopharmaceutical has fast blood clearance and prominent hepatic uptake. As shown in FIG. 6, the radiotracer accumulates in breast tumors. Interestingly, $^{99m}$Tc-Mito-MAG3 exhibited significant focal uptake in small breast tumors that escaped detection by palpation.

In particular, referring to FIG. 8, tumors that are undetectable by palpation are shown and labeled as B and D. Also, a large primary tumor (necrotic) is shown and labeled as C and another large primary tumor is shown and labeled as C.

Conclusion. $^{99m}$Tc-Mito-MAG3 is taken up by tumors that appear to be metabolically active, consistent with its mitochondria-targeting activity. The radiotracer can detect tumors at an early stage below the detection threshold of palpation.

$^{99m}$Tc-Mito$_{10}$-MAG3 accumulates in metabolically active breast tumors. The radiotracer detects small breast tumors that were missed by palpation. An example is illustrated in FIG. 6 (18 mg tumor at the left anterior). The sensitivity of current clinical imaging (FDG-PET, MIBI-SPECT) for breast cancer is poor for tumors smaller than 7-8 mm in diameter (~800 mg in weight).

Methods. Mito$_{10}$-MAG3 was synthesized by coupling (10-aminodecyl)triphenyl phosphonium bromide with NHS-MAG3, and radiolabeled with $^{99m}$Tc. Biodistribution and pharmacokinetics of $^{99m}$Tc-Mito$_{10}$-MAG3 were determined in female Sprague Dawley rats. Initially, $^{99m}$Tc-Mito$_{10}$-MAG3 was tested in animals with established breast tumors. In a subsequent longitudinal study, the imaging efficacy of $^{99m}$Tc$_{10}$-Mito-MAG3 for detecting small, non-palpable breast tumors was assessed after chemically inducing breast carcinoma. Tumors detected by imaging were allowed to grow to a palpable size and were confirmed by histology. The results were compared with $^{99m}$Tc-MIBI.

Results. The synthesis of Mito$_{10}$-MAG3 was confirmed by mass spectrometry. The compound was radiolabeled with $^{99m}$Tc to >92% in a single step. The radiopharmaceutical exhibited fast blood clearance and low cardiac uptake. In the initial study using animals with established breast tumors, $^{99m}$Tc-Mito$_{10}$-MAG3 imaging detected small lesions that were missed by palpation. In the longitudinal study, $^{99m}$Tc-Mito$_{10}$-MAG3 exhibited focal uptake in small breast tumors, which was confirmed by histology.

Conclusion. $^{99m}$Tc-Mito$_{10}$-MAG3 exhibits focal uptake in small neoplastic lesions in the mammary glands prior to detection by palpation. The phosphonium-based derivatives warrant further characterization and development as imaging agents for scintimammography.

Example 2

Synthesis of Mito$_{10}$-MAG3.

All reagents were used as received without further purification. The reactions were monitored by thin layer chromatography (TLC) on silica gel and by high performance liquid chromatography (HPLC). Crude materials were purified by flash chromatography on silica gel 60 (0.040-0.063 mm). Characterization was performed on HPLC and high resolution mass spectrometry (HRMS) for all products. HPLC experiments were performed using an Agilent 1100 system equipped with UV-Vis absorption and fluorescence detectors using a $C_{18}$ column (Alltech, Kromasil, 250×4.6 mm, 5 μm) that was equilibrated with 10% $CH_3CN$ (containing 0.1% (v/v) trifluoroacetic acid (TFA)) in 0.1% TFA aqueous solution. Approximately 40 min after injection, the $CH_3CN$ fraction was increased to 100% and the compounds were eluted using a flow rate of 0.5 ml/min. Mass spectra were obtained using the 7.0 Tesla Fourier Transform Ion Cyclotron Resonance (FTICR) Mass Spectrometer-interfaced with an Agilent 1100 HPLC system.

Mito$_{10}$-MAG3 was synthesized according to the protocol depicted in FIG. 4. N-hydroxysuccinamide ester activated mercaptoacetyltriglycine (NHS-MAG3) was synthesized as describe before with minor modifications [30].

i) (10-phtalimidyl) triphenylphosphonium bromide (1). A mixture containing bromodecyl phtalimide (7 g, 0.019 mol) and triphenylphosphine (5 g, 0.019 mol) in acetonitrile (60 mL) was refluxed for 15 hours. The solvent was distilled under reduced pressure. The crude product was purified by flash chromatography on silica gel ($CH_2Cl_2$/EtOH 80:20) afforded a white solid 1 (9 g, 73%). MS calcd for $[C_{36}H_{39}NO_2P]^+$, Br$^-$; $[C_{36}H_{39}NO_2P]^+$, 548.3, found: 548.3.

ii) (10-aminodecyl)triphenylphosphonium bromide (2). To a solution of 1 (7 g, 0.0108 mol) in EtOH (70 mL) was added hydrazine (0.54 mL, 0.0108 mol). The mixture was refluxed for 15 hours. The solvent was distilled and the impurity was crystallized using a mixture $Et_2O$/EtOH (100 mL+45 mL). The product was purified by flash chromatography on a silicagel ($CH_2Cl_2$/EtOH 80:20) afforded a yellow solid 2 (4 g, 73%). $^{31}$P NMR (121.49 MHz) δ 24.61. $^1$H NMR (300.13 MHz) δ 7.95-7.73 (15H, m), 3.70-3.55 (2H, m), 2.80-2.70 (2H, m), 1.60-1.40 (6H, m), 1.35-1.10 (10H, m). MS calcd for $[C_{28}H_{37}NP]^+$, Br$^-$; $[C_{28}H_{37}NP]^+$, 418.2, found: 418.2.

iii) Mito-MAG3 (3). To a mixture of NHS-MAG3 (0.100 g, 0.25 mmol) and (10-aminodecyl)triphenylphosphonium bromide 2 (0.123 g, 0.25 mmol) in DMSO (10 mL) was added at room temperature under inert atmosphere triethylamine (82

μL, 0.60 mmol). The reaction mixture was stirred for 12 h, and then the solvent was distilled under high vacuum. Purification of the crude product by preparative HPLC using a $C_{18}$ column afforded a white powder (0.097 g, 50%), corresponding to Mito-MAG33. HRMS calcd for $C_{38}H_{50}N_4O_5PS$, $[C_{38}H_{50}N_4O_5PS]^+$: 705.3229 found: 705.1130. HPLC, 33.58 min.

Radiolabeling of $Mito_{10}$-MAG3.

$Mito_{10}$-MAG3 was radiolabeled with $^{99m}Tc$, using a protocol previously reported with minor modifications [30]. Specifically, an aliquot of $Mito_{10}$-MAG3 (30 μg) was re-suspended in 450 μl of freshly prepared labeling solution containing 7.5 mg tartaric acid, 9.5 mg ammonium acetate, 10 μg stannous chloride, pH 8.3. After the addition of $^{99m}Tc$ pertechnetate (3 mCi), the labeling mixture was incubated at 65° C. for one hour. For quality control purposes, the radiolabeled product was routinely analyzed by radioHPLC (4.6× 250 mm $C_{18}$ reversed phase column) at room temperature, with the following method.

Buffer A contained 10 mM phosphate buffer (pH 6.8) and buffer B contained 100% acetonitrile. A baseline of 90% A and 10% B was run for 10 min, followed by a linear gradient with the mobile phase reaching 10% A and 90% B at 40 min. To determine the radio-stability, the radiopharmaceutical was maintained in physiological buffer for up to 48 hours, and the radiochemical purity was examined by radioHPLC.

Biodistribution and Pharmacokinetics in Rats.

$^{99m}Tc$-$Mito_{10}$-MAG3 was injected into healthy rats (female Sprague Dawley, 250-300 g) via the tail vein. Rats (n=3) were sacrificed at 1, 3, 5, 10, 30 and 60 min after injection and the distribution of radioactivity in different tissues was determined by gamma well counting with an energy window of 140±15 keV. The biodistribution data is expressed in terms of percentage injected dosage per gram (% ID/g) with mean±standard deviation. Urine samples were collected from the bladder at 30 min after injection, and were analyzed by radioHPLC to determine the presence of metabolic derivatives of the radiotracer. Tracer kinetics and biodistribution profile were confirmed using in vivo scintigraphic imaging. Specifically, anterior planar whole-body dynamic images were acquired on an XRT gamma camera (General Electric) using a high-resolution medium energy parallel-hole collimator at one frame per minute for 60 min, with 512×512 matrix, and an energy window of 140±15 keV.

In vivo studies using a chemically induced breast tumor model in rats.

The animal protocol was approved by institutional IACUC review and followed NIH guidelines. The rat model of DMBA-induced breast carcinoma was used.

As an initial feasibility study, rats were induced with 65 mg/kg DMBA dissolved in sesame oil via a single oral gavage to the stomach. Eleven weeks later, three rats with established breast carcinoma (0.5 to 1.9 cm in diameter) were imaged after $^{99m}Tc$-$Mito_{10}$-MAG3 injection (10 μg, 1 mCi) using a constant rate infusion pump for a total injection volume of 150 μl over a period of 35 min. Static images were acquired on a GE XRT gamma camera using a high-resolution parallel-hole collimator, 512×512 matrix size, 22.5×22.5 cm field of view, 140±15 keV energy window, 100 k counts. Unexpectedly, apart from the established palpable carcinomas, additional small (millimeter size) tumors were discovered by this imaging technique in the same animals. This finding promoted a longitudinal study to investigate the early detection of neoplastic growth using $^{99m}Tc$-$Mito_{10}$-MAG3.

Six 48-day-old female rats were injected with 65 mg/kg DMBA. At each week after DMBA induction, the rats were imaged using the following protocol. Each rat was anesthetized with 1.6% isoflurane in room air supplemented with oxygen. The rat was immobilized in a prone position on the surface of the gamma camera. $^{99m}Tc$-$Mito_{10}$-MAG3 (10 μg, 1 mCi) was injected via the tail vein using a constant rate infusion pump for a total injection volume of 150 μl over a period of 35 min. Dynamic images were continuously acquired at one frame per min for 90 min using the imaging parameters set forth hereinabove. The weekly imaging regiment was continued for all six rats until palpable tumors became detectable, which typically takes place between seven to nine weeks after the administration of DMBA. Due to the relatively short physical half-life of $^{99m}Tc$ (6 hr), no residual signal, therefore, no cross-contamination is detectable from the previous injection the week before.

Comparative Data: Comparison of $^{99m}Tc$-$Mito_{10}$-MAG3 and $^{99m}Tc$-MIBI.

$^{99m}Tc$-MIBI of clinical formulation was purchased from Bristol Myers Squibb. At 48 hours after the breast tumors were first identified using $^{99m}Tc$-$Mito_{10}$-MAG3, the same rats were injected with $^{99m}Tc$-MIBI (1 mCi per rat) via the tail vein. At this time, the radioactivity from the $^{99m}Tc$-$Mito_{10}$-MAG3 injection already had cleared to background from the animals due to physical decay and excretion. Dynamic images were acquired in identical fashion following $_{99m}Tc$-MIBI injection.

Imaging Data Analysis.

The female Sprague Dawley rats have six pairs of mammary glands, among which glands a and b are away from the hepatic/gastrointestinal region. (FIG. 9, Panel A). Since the typical biodistribution of a lipophilic radiopharmaceutical in the abdominal region precludes reliable imaging of breast tissues below the diaphragm, mammary glands shown in Panels C, D, E and F were excluded from the data analysis. This exclusion also was based on the fact that such spatial distribution of mammary glands is irrelevant to that of the human anatomy.

Imaging data analysis was carried out using an inbuilt software, by carefully drawing a region of interest (ROI) on the tumor site to determine the radioactivity counts in the ROI. ROIs with identical geometry and number of pixels were positioned on the contralateral normal mammary gland and the thigh muscle. Radioactivity counts were determined in each ROI. Tumor-to-normal and tumor-to-muscle ratios were calculated as the count ratio between the two ROIs.

Histology.

The rats were sacrificed by $CO_2$ asphyxiation and the number and location of the mammary tumors were recorded at necropsy. The tumors were dissected, with the diameter and weight measured and documented. Portions of each tumor were fixed in 10% formalin and embedded in paraffin. Histological sections, at 5 μm thick, were prepared and stained with H&E according to standard histological protocol. Pathologic diagnoses of the mammary lesions were classified by a certified pathologist.

Results.

Synthesis and characterization of $Mito_{10}$-MAG3.

The chemical yield and molecular weights (MW) of the intermediates and final compound are as follows. 1. yield 73%; calculated MW for $[C_{36}H_{39}NO_2P]^+$, $Br^-$; $[C_{36}H_{39}NO_2P]^+$, 548.3, found: 548.3. 2. yield 73%; calculated MW for $[C_{28}H_{37}NP]^+$, $Br^-$; $[C_{28}H_{37}NP]^+$, 418.2, found: 418.2. 3. yield 50%; calculated MW for $C_{38}H_{50}N_4O_5PS$, $[C_{38}H_{50}N_4O_5PS]^+$: 705.3229 Found: 705.1130. The structure of $Mito_{10}$-MAG3 was confirmed by $^{31}P$ and $^1H$ NMR with the following findings. $^{31}P$ NMR (121.49 MHz) δ 24.27. $^1H$ NMR (300.13 MHz) δ 9.05 (1H, t, J=5.3), 8.31 (1H, t, J=5.8), 8.18 (1H, t, J=6.6), 7.90-7.62 (15H, m), 7.06 (1H, t, J=5.5), 3.98 (2H, d, J=5.8), 3.82 (4H, 2d, J=6.6, 5.3), 3.67 (s, 2H), 3.40-3.28 (2H, m), 3.21 (2H, q, J=6.4, 12:6), 2.35 (3H, s), 1.60-1.45 (6H, m), 1.35-1.20 (10H, m). The NMR spectra are included in the Supporting Information.

Radiolabeling.

Mito$_{10}$-MAG3 was labeled with $^{99m}$Tc to relatively high radiochemical purity and yield in a single step. According to radioHPLC analysis, the radiochemical purity was consistently greater than 92%. At the current labeling condition, the specific activity was about 100 Ci/g. Once labeled, the radiopharmaceutical was stable in physiological solution for an extended period of time without degradation. This was confirmed using radioHPLC, where the percentage of radioactivity bound to Mito$_{10}$-MAG3 remained persistent for at least 48 hours after labeling.

Biodistribution and Pharmacokinetics.

In a comparative study, the myocardial uptake of $^{99m}$Tc-MIBI peaked at 2.70±0.4% ID/g within minutes after injection, and remained above 2.41±0.3% ID/g for at least 90 min. Comparatively, the myocardial uptake level of $^{99m}$Tc-Mito$_{10}$-MAG 3 is 10, 40, and 120 fold lower than the uptake level of $^{99m}$Tc-MIBI at 3, 10 and 30 min after injection. The hepatic uptake of $^{99m}$Tc-MIBI was at 0.37±0.14% ID/g at 30 min after injection.

In vivo imaging of chemically induced tumors in a rat breast cancer model.

In a feasibility experiment, three rats having established breast carcinomas (average size 0.5-1.9 cm in diameter) were

TABLE 1

Biodistribution of $^{99m}$Tc-Mito$_{10}$-MAG3 in rats in terms of % ID/g

| Organ | Radioactivity Uptake (% ID/g) | | | | | |
|---|---|---|---|---|---|---|
| | 1 min | 3 min | 5 min | 10 min | 30 min | 60 min |
| Brain | 0.04 ± 0.03 | 0.02 ± 0.01 | 0.04 ± 0.03 | 0.01 ± 0.00 | 0.01 ± 0.01 | 0.00 ± 0.00 |
| Thyroid | 0.30 ± 0.13 | 0.33 ± 0.07 | 0.27 ± 0.11 | 0.11 ± 0.04 | 0.02 ± 0.02 | 0.01 ± 0.00 |
| Lung | 0.82 ± 1.05 | 0.31 ± 0.14 | 0.48 ± 0.43 | 0.23 ± 0.24 | 0.05 ± 0.01 | 0.03 ± 0.01 |
| Heart | 0.20 ± 0.08 | 0.27 ± 0.04 | 0.18 ± 0.07 | 0.06 ± 0.01 | 0.02 ± 0.02 | 0.01 ± 0.00 |
| Liver | 3.23 ± 1.10 | 2.41 ± 1.12 | 1.50 ± 0.84 | 0.89 ± 0.30 | 0.32 ± 0.02 | 0.21 ± 0.07 |
| Pancreas | 0.32 ± 0.22 | 0.27 ± 0.12 | 0.20 ± 0.17 | 0.12 ± 0.04 | 0.01 ± 0.00 | 0.02 ± 0.01 |
| Spleen | 0.27 ± 0.12 | 0.25 ± 0.17 | 0.20 ± 0.08 | 0.09 ± 0.04 | 0.02 ± 0.02 | 0.02 ± 0.01 |
| Kidneys | 2.30 ± 0.55 | 3.69 ± 0.92 | 3.06 ± 1.41 | 1.79 ± 0.39 | 1.40 ± 0.96 | 0.75 ± 0.59 |
| Stomach | 0.26 ± 0.04 | 0.32 ± 0.12 | 0.25 ± 0.26 | 0.30 ± 0.24 | 0.57 ± 0.41 | 0.04 ± 0.05 |
| Small Intestine | 0.18 ± 0.04 | 0.67 ± 0.30 | 0.48 ± 0.14 | 0.50 ± 0.19 | 0.52 ± 0.20 | 0.36 ± 0.41 |
| Colon | 0.09 ± 0.04 | 0.08 ± 0.03 | 0.02 ± 0.01 | 0.03 ± 0.01 | 0.04 ± 0.03 | 0.01 ± 0.00 |
| Bone[1] | 0.12 ± 0.05 | 0.05 ± 0.01 | 0.02 ± 0.24 | 0.04 ± 0.03 | 0.01 ± 0.01 | 0.00 ± 0.00 |
| Muscle[1] | 0.05 ± 0.02 | 0.03 ± 0.01 | 0.06 ± 0.01 | 0.06 ± 0.01 | 0.02 ± 0.01 | 0.01 ± 0.00 |
| Fat[1] | 0.04 ± 0.02 | 0.06 ± 0.01 | 0.07 ± 0.05 | 0.07 ± 0.03 | 0.01 ± 0.00 | 0.00 ± 0.00 |
| Skin | 0.07 ± 0.03 | 0.10 ± 0.04 | 0.12 ± 0.08 | 0.05 ± 0.04 | 0.04 ± 0.03 | 0.02 ± 0.01 |
| Thymus | 006 ± 0.02 | 0.12 ± 0.04 | 0.07 ± 0.01 | 0.04 ± 0.03 | 0.01 ± 0.00 | 0.01 ± 0.00 |
| Urine[1] | 0.05 ± 0.05 | 0.76 ± 0.56 | 0.68 ± 0.03 | 2.35 ± 2.63 | 8.83 ± 8.50 | 10.85 ± 12.48 |

Note:
Each data point represents the mean uptake with standard deviation from three animals.
[1]Non-organ The intravenous injection of $^{99m}$Tc-Mito$_{10}$-MAG3 was followed with a prompt blood clearance, where the blood half-life was estimated to be less than 2 min. Importantly, the myocardial uptake of the tracer was relatively low, peaking at 0.27±0.04% ID/g at 3 min after injection. (Table 1). A continuous washout reduced the myocardial radioactivity level to 0.06±0.01 and 0.02±0.02% ID/g at 10 min and 30 min after injection. Other tissues in the thoracic region (including the lungs) muscle, thymus, thyroid, and bones were low in radioactivity uptake. The bulk of the injected dosage was initially collected in the liver and the kidneys, where hepatic and renal clearance were the main routes of clearance. (Table 1). Once taken up in the liver, the radioactivity rapidly transit to the gastrointestinal tract, accompanied with a fast decline of hepatic signal from 3.23±1.10% ID/g at 1 min to 0.32±0.02% ID/g at 30 min after injection. (Table 1). The biodistribution profile was confirmed by whole-body dynamic imaging, where the radiotracer rapidly cleared from the hepatic/gastrointestinal and renal/urinary systems, leaving a low general background. The metabolized radioactive species of the radiopharmaceutical were detected in urine samples by radio-HPLC. (FIG. 2).

imaged with $^{99m}$Tc-Mito$_{10}$-MAG3 at 11 weeks after DMBA induction. Unexpectedly, apart from the known tumor sites at mammary glands Rc and Rf, two well-defined focal uptake of the radiotracer were detected in the same animals at mammary glands La and Re. (FIG. 8). Histological analysis confirmed the presence of papillary carcinoma at La, Rc, and Rf, and, the mammary tissue from the contra lateral side (gland Le) was used as control. (FIG. 8 Panel E). The size of the small tumor at Ra at the time of dissection was 2.5×5.9×1.9 mm, weighing 18 mg. A focal radioactivity uptake at Re (but histological equivocal) site was marked with a block arrow. In light of these findings, a longitudinal experiment focusing on detecting breast carcinoma at an early growth phase was performed.

In the longitudinal experiment, of the six rats enrolled, four sites of neoplastic growth were induced in mammary glands a and b. Using $^{99m}$Tc-Mito$_{10}$-MAG3, all four tumors were detected as focal radioactivity uptake at least one week earlier than by palpation. The tumor-to-normal and tumor-to-muscle ratios were 2.39±0.77 and 6.61±1.74, respectively, at the time of detection. This ratio was similar to that obtained by $^{99m}$Tc-MIBI injection (2.04±0.49 and 5.10±0.31). The suspicious sites were allowed to develop until the carcinomas became detectable by palpation. Postmortem histological analysis confirmed the presence of breast tumors. Of the four sites, three were papillary carcinoma, and one was atypical in situ ductal hyperplasia. A typical example of in vivo imaging and the corresponding histology is demonstrated in FIG. 9. Consecutive weekly imaging results are shown in FIG. 9 Panels A, B and C, where elevating radioactivity uptake at the site of tumor development is marked by an arrow. The presence of papillary carcinoma at the right mammary gland "a" was confirmed by H&E stained histology, which demonstrates the gross tumor morphology and cellular carcinogenesis (at a higher magnification) in FIG. 9 Panels D and E, respectively.

We claim:

1. A compound according to the structure:

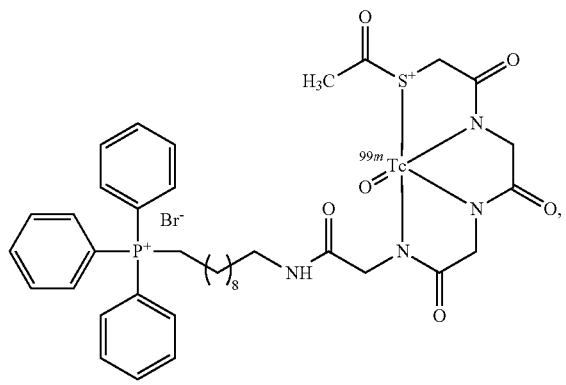

or a solvate or hydrate thereof.

2. A process of making the compound of claim 1 comprising:

providing a compound according to the structure:

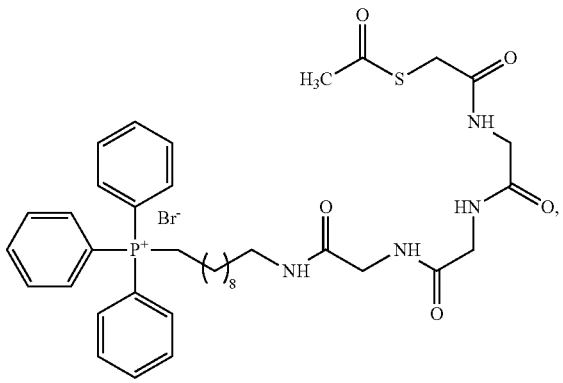

or a solvate or hydrate thereof, and radiolabeling the compound by chelating the compound with a radioisotope-containing reactant comprising $^{99m}$Tc.

3. The process of claim 2, wherein the radioisotope-containing reactant comprises $^{99m}$Tc pertechnetate.

4. An injectable dosage form comprising the compound of claim 1 and a pharmaceutically suitable injectable carrier system.

5. A method of detecting breast cancer in a female human patient in need thereof comprising:
   injecting an injectable dosage form comprising the compound of claim 1 and a pharmaceutically suitable injectable carrier system, and,
   scintimammographically imaging the radioactivity of the radioisotope.

* * * * *

UNITED STATES PATENT AND TRADEMARK OFFICE
CERTIFICATE OF CORRECTION

PATENT NO. : 8,388,931 B2
APPLICATION NO. : 12/394581
DATED : March 5, 2013
INVENTOR(S) : Lopez et al.

It is certified that error appears in the above-identified patent and that said Letters Patent is hereby corrected as shown below:

In the Specifications

Column 8, Line 8 "Biochinica" should read -- Biochimica --

Signed and Sealed this
Ninth Day of July, 2013

Teresa Stanek Rea
*Acting Director of the United States Patent and Trademark Office*